US009725741B2

(12) United States Patent
Biton et al.

(10) Patent No.: US 9,725,741 B2
(45) Date of Patent: *Aug. 8, 2017

(54) RECOMBINANT BACTERIA AND THE USES THEREOF FOR PRODUCING ETHANOL

(71) Applicant: DEINOVE, Grabels (FR)

(72) Inventors: Jacques Biton, Lacroix-Saint-Ouen (FR); Esther Gerber, Prades le Lez (FR)

(73) Assignee: DEINOVE, Grabels (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/713,248

(22) Filed: May 15, 2015

(65) Prior Publication Data

US 2015/0247167 A1    Sep. 3, 2015

Related U.S. Application Data

(63) Continuation of application No. 13/319,526, filed as application No. PCT/EP2010/056592 on May 12, 2010, now Pat. No. 9,034,619.

(30) Foreign Application Priority Data

May 14, 2009  (EP) .................................. 09160284

(51) Int. Cl.
    *C12N 15/74*    (2006.01)
    *C12P 7/06*     (2006.01)
    *C12N 9/04*     (2006.01)
    *C12N 9/88*     (2006.01)

(52) U.S. Cl.
    CPC ............ *C12P 7/065* (2013.01); *C12N 9/0006* (2013.01); *C12N 9/88* (2013.01); *C12N 15/74* (2013.01); *C12Y 101/01001* (2013.01); *C12Y 401/01001* (2013.01); *Y02E 50/17* (2013.01)

(58) Field of Classification Search
    CPC ................................ C12N 9/0006; C12N 9/88
    USPC ............................................. 435/161, 252.3
    See application file for complete search history.

(56) References Cited

U.S. PATENT DOCUMENTS

| 5,000,000 | A | 3/1991 | Ingram et al. |
| 6,102,690 | A | 8/2000 | Ingram et al. |
| 8,728,777 | B2 | 5/2014 | Biton et al. |
| 9,005,954 | B2 | 4/2015 | Leonetti et al. |
| 9,034,619 | B2 * | 5/2015 | Biton ................... C12N 9/0006 435/161 |
| 2011/0104766 | A1 | 5/2011 | Leonetti et al. |
| 2011/0294979 | A1 | 12/2011 | Leonetti et al. |
| 2011/0306085 | A1 | 12/2011 | Isop et al. |
| 2012/0052540 | A1 | 3/2012 | Biton et al. |
| 2014/0017724 | A1 | 1/2014 | Leonetti et al. |

FOREIGN PATENT DOCUMENTS

| EP | 2218773 | 8/2010 |
| EP | 1 322 775 | 5/2011 |
| JP | 2004-510435 | 4/2004 |
| JP | 2004-344107 | 12/2004 |
| KR | 100836093 | 6/2008 |
| WO | WO 95/27064 | 10/1995 |
| WO | WO 97/10352 | 3/1997 |
| WO | WO 01/23526 | 4/2001 |
| WO | WO 02/059351 | 8/2002 |
| WO | WO 2006/131734 | 12/2006 |
| WO | WO 2007/128338 | 11/2007 |
| WO | WO 2009/063079 | 5/2009 |
| WO | WO 2010/081899 | 7/2010 |
| WO | WO 2010/094665 | 8/2010 |
| WO | WO 2010/130812 | 11/2010 |
| WO | WO2011/107506 | 9/2011 |

OTHER PUBLICATIONS

Lu, J., "Cloning of Zymomonas Mobilis Alcohol Dehydrogenase and Pyruvate Decarboxylase and Their Expression in *Escherichia Coli*," edited and published by *Chinese Academic Journal (CD) Electronic Magazine*, Master's Thesis, Database of Excellent Theses of Doctor and Master degree of China, 2002, Issue 2, pp. 1-16.
Yi, L., "A new addition to the biological sewage bacteria *Deinococcus radiodurans*," *Foreign Medical Sciences (Section Hygiene)*, Third Military Medical University, Department of Environmental Health, Department of Prevention, Chongqing, China, 2003, vol. 30, No. 3, pp. 1-6.
Zhang, Y.-M. et al. "Induction of a Futile Embden-Meyerhof-Parnas Pathway in *Deinococcus radiodurans* by Mn: Possible Role of the Pentose Phosphate Pathway in Cell Survival" *Applied and Environmental Microbiology*, Jan. 2000, pp. 105-112, vol. 66, No. 1.
Holland, A. et al. "Development of a defined medium supporting rapid growth for *Deinococcus radiodurans* and analysis of metabolic capacities" *Applied Microbiology and Biotechnology*, Mar. 31, 2006, pp. 1074-1082, vol. 72, No. 5.
Anonymous. "Conference de presse: Présentation des projets de DEINOVE dans le domaine des biocarburants et des activités de DEINOLAB, laboratoire coopératif créé par DEINOVE, le CNRS et l'Université de Montpellier" Oct. 15, 2008, pp. 1-10, XP-002591932.
Written Opinion in International Application No. PCT/EP2010/056592, Jul. 29, 2010, pp. 1-7.
Harish, V. et al. "Xylanase Production by Ultra Violet Induced Variants of *Streptomyces fradiae* SCF-5" *Journal of Food Science and Technology*, Jan. 1, 1978, pp. 243-246, vol. 15, No. 6.

(Continued)

*Primary Examiner* — Tekchand Saidha
(74) *Attorney, Agent, or Firm* — Saliwanchik, Lloyd & Eisenschenk

(57) ABSTRACT

The present invention relates to recombinant bacteria and the uses thereof, particularly for the production of ethanol. The invention also relates to methods for the production of such bacteria, as well as to nucleic acid constructs suitable for such production. The invention specifically relates to bacteria lacking a functional LDH gene and/or containing a recombinant nucleic acid encoding a PDC and ADH. The bacteria of this invention may be produced from any stress-resistant bacteria.

Figure 1:
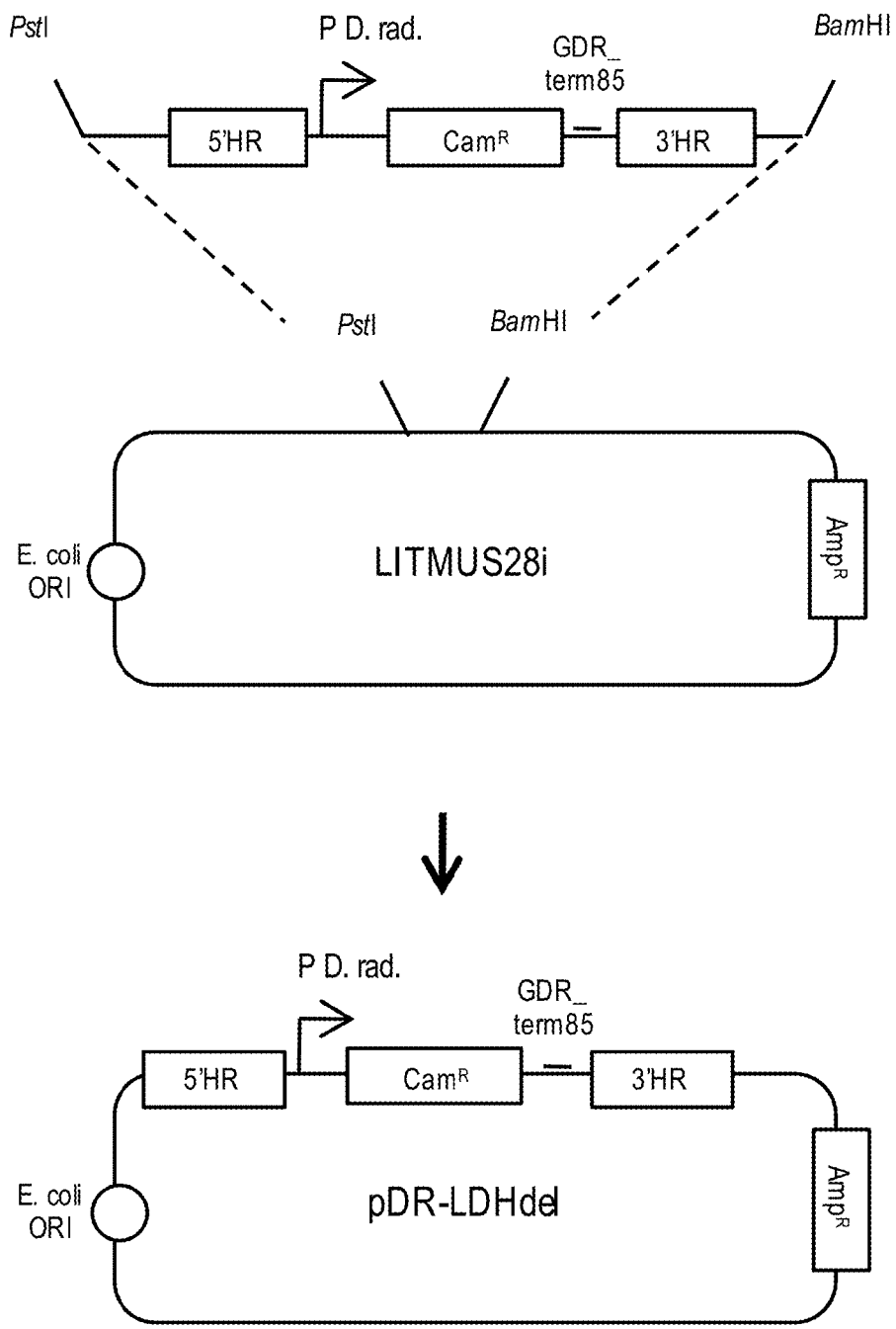

23 Claims, 9 Drawing Sheets
(1 of 9 Drawing Sheet(s) Filed in Color)

(56) References Cited

OTHER PUBLICATIONS

Alea, F. et al. "Selection of hypercellulolytic derepressed mutants of *Cellulomonas* sp." *Applied Microbiology and Biotechnology*, 1991, pp. 643-645, vol. 35, No. 5.

Temp, U. et al. "A Small-Scale Method for Screening of Lignin-Degrading Microorganisms" *Applied Environmental Microbiology*, Apr. 1998, pp. 1548-1549, vol. 64, No. 4.

Zenoff, V. F. et al. "Diverse UV-B Resistance of Culturable Bacterial Community from High-Altitude Wetland Water" *Current Microbiology*, May 1, 2006, pp. 359-362, vol. 52, No. 5.

Pavlikova, E. et al. "Improvement of the Basidiomycete *Coprinus* sp." *Folia Microbiologica*, Jan. 1, 1982, pp. 126-130, vol. 27, No. 2.

Written Opinion in International Application No. PCT/EP2010/051885, Aug. 23, 2010, pp. 1-10.

Makarova, K. et al. "Genome of the Extremely Radiation-Resistant Bacterium *Deinococcus radiodurans* Viewed from the Perspective of Comparative Genomics" *Microbiology and Molecular Biology Reviews*, Mar. 2001, pp. 44-79, vol. 65, No. 1.

Omelchenko, M. et al. "Comparative genomics of *Thermus thermophilus* and *Deinococcus radiodurans*: divergent routes of adaptation to thermophily and radiation resistance" *BMC Evolutionary Biology*, 2005, pp. 1-22, vol. 5, No. 57.

Rainey, F. et al. "Extensive Diversity of Ionizing-Radiation-Resistant Bacteria Recovered from Sonoran Desert Soil and Description of Nine New Species of the Genus *Deinococcus* Obtained from a Single Soil Sample" *Applied and Environmental Microbiology*, Sep. 2005, pp. 5225-5235, vol. 71, No. 9.

Weisburg, W.G. et al. "The *Deinococcus-Thermus* Phylum and the Effect of rRNA Composition on Phylogenetic Tree Construction" *Systematic and Applied Microbiology*, 1989, pp. 128-134, vol. 11.

Database EMBL, Accession No. M21413, "D. radiodurans 16s ribosomal RNA gene" XP002633260, Nov. 23, 1989, p. 1.

Suihko, M.L. et al. "Characterization of aerobic bacterial and fungal microbiota on surfaces of historic Scottish monuments" *Systematic and Applied Microbiology*, 2007, pp. 494-508, vol. 30.

Database EMBL, Accession No. EF093134, "*Deinococcus sp.* VTT E-052909 16S ribosomal RNA gene, complete sequence" XP002633261, Aug. 7, 2007, pp. 1-2.

Database EMBL, Accession No. AM283039, "*Deinococcus sp.* Han23 partial 16S rRNA gene, strain Han23" XP002633262, Jun. 26, 2006, p. 1.

Rainey, F. et al. "Phylogenetic Diversity of the *Deinococci* as Determined by 16S Ribosmal DNA Sequence Comparison" *International Journal of Systemic Bacteriology*, Apr. 1997, pp. 510-514, vol. 47, No. 2.

Written Opinion in International Application No. PCT/EP2011/053089, Mar. 2, 2010, pp. 1-7.

Brim, H. et al. "Engineering *Deinococcus radiodurans* for metal remediation in radioactive mixed waste environments" *Nature Biotechnology*, Jan. 2000, pp. 85-90, vol. 18, XP-002491111.

Henstra, A. M. et al. "Microbiology of synthesis gas fermentation for biofuel production" *Current Opinion in Biotechnology*, 2007, pp. 200-206, vol. 18, XP-22110181.

John, R. P. et al. "Fermentative production of lactic acid from biomass: an overview on process developments and future perspectives" *Appl. Microbiol. Biotechnol.*, 2007, pp. 524-534, vol. 74, XP-002464997.

Klapatch, T. R. et al. "Organism Development and Characterization for Ethanol Production Using Thermophilic Bacteria" *Applied Biochemistry and Biotechnology*, 1994, pp. 209-223, vol. 45/46, XP-009104255.

Lynd, L. R. "Production of Ethanol from Lignocellulosic Materials Using Thermophilic Bacteria: Critical Evaluation of Potential and Review" *Advances in Biochemical Engineering*, 1989, pp. 1-52, vol. 38, XP-9104256.

Makarova, K. S. et al. "*Deinococcus geothermalis*: The Pool of Extreme Radiation Resistance Genes Shrinks" *PLOS ONE*, Sep. 2007, pp. 1-21, vol. 9, XP-002491112.

Meima, R. et al. "Promoter Cloning in the Radioresistant Bacterium *Deinococcus radiodurans*" *Journal of Bacteriology*, May 2001, pp. 3169-3174, vol. 183, No. 10, XP-002491110.

Smith, M. D. et al. "Gene expression in *Deinococcus radiodurans*" *Gene*, 1991, pp. 45-52, vol. 98, XP-002938523.

Zahradka, K. et al. "Reassembly of shattered chromosomes in *Deinococcus radiodurans*" *Nature*, Oct. 5, 2006, pp. 569-573, vol. 443, XP-002491114.

Office Action dated Nov. 8, 2012 in U.S. Appl. No. 12/740,404.

Fontaine, L. et al. "Molecular Characterization and Transcriptional Analysis of *adhE2*, the Gene Encoding the NADH-Dependent Aldehyde/Alcohol Dehydrogenase Responsible for Butanol Production in Alcohologenic Cultures of *Clostridium acetobutylicum* ATCC 824" *Journal of Bacteriology*, Feb. 2002, pp. 821-830, vol. 184, No. 3.

Skory, C. D. "Isolation and Expression of Lactate Dehydrogenase Genese from *Rhizopus oryzae*" *Applied and Environmental Microbiology*, Jun. 2000, pp. 2343-2348, vol. 66, No. 6.

Berdy, J. "Bioactive Microbial Metabolites—A personal view" *Journal of Antibiotics*, Jan. 1, 2005, pp. 1-26, vol. 58, No. 1.

Singh, S. et al. "Biodiversity, chemical diversity and drug discovery" *Progress in Drug Research*, 2008, pp. 142-174, vol. 65.

Yang, B. et al. "Effects of microwave irradiation on isolation of soil actinomycetes" *Yingyong Shengtai Xuebao*, May 2008, pp. 1091-1098, vol. 19, No. 5.

Sinha, R. et al. "UV-protectants in cyanobacteria" *Plant Science*, Dec. 23, 2007, pp. 278-289, vol. 174, No. 3.

Chung, B. et al. "Effects of low-dose gamma-irradiation on production of shikonin derivatives in callus cultures of *Lithospermum erythrorhizon* S." *Radiation Physics and Chemistry*, Sep. 1, 2006, pp. 1018-1023, vol. 75, No. 9.

Ghosal, D. et al. "How radiation kills cells: Survival of *Deinococcus radiodurans* and *Shewanella oneidensis* under oxidative stress" *FEMS Microbiology Reviews*, Apr. 2005, pp. 361-375, vol. 29.

Dib, J. et al. "Occurrence of Resistance to Antibiotics, UV-B, and Arsenic in Bacteria Isolated from Extreme Environments in High-Altitude (Above 4400 m) Andean Wetlands" *Current Microbiology*, May 2008, pp. 510-517, vol. 56, No. 5.

Keller, M. et al. "Tapping Into Microbial Diversity" *Nature Reviews*, Feb. 2004, pp. 141-150, vol. 2, No. 2.

Reichenbach, H. "Myxobacteria, producers of novel bioactive substances" *Journal of Industrial Microbiology & Biotechnology*, Jan. 1, 2001, pp. 149-156, vol. 27. No. 3.

Bibb, M. "Regulation of secondary metabolism in streptomycetes" *Current Opinion in Microbiology*, 2005, pp. 208-215, vol. 8, No. 2.

Written Opinion in International Application No. PCT/EP2010/050513, Apr. 24, 2010, pp. 1-10.

Kolari, M. et al. "Colored moderately thermophilic bacteria in paper-machine biofilms" *Journal of Industrial Microbiology and Biotechnology*, Apr. 2003, pp. 225-238, vol. 30, No. 4.

Written Opinion in International Application No. PCT/EP2010/056600, May 14, 2009, pp. 1-8.

Ferreira, A. et al. "*Deinococcus geothermalis* sp. nov. and *Deinococcus murrayi* sp. nov., Two Extremely Radiation-Resistant and Slightly Thermophilic Species from Hot Springs" *International Journal of Systematic Bacteriology*, Oct. 1997, pp. 939-947, vol. 47, No. 4.

Weon, H. et al. "*Deinococcus cellulosilyticus* sp. nov., isolated from air" *International Journal of Systematic and Evolutionary Microbiology*, Aug. 1, 2007, pp. 1685-1688, vol. 57, No. Part 8.

Written Opinion in International Application No. PCT/EP2008/065613, Jan. 28, 2009, pp. 1-8.

Office Action dated Jan. 7, 2013 in U.S. Appl. No. 13/145,246.

Office Action dated Jan. 2, 2013 in U.S. Appl. No. 13/320,048.

Cox, M. et al. "*Deinococcus Radiodurans*—The Consummate Survivor" *Nature Reviews in Microbiology*, Nov. 2005, pp. 882-892, vol. 3.

Panesar, P. et al. "Comparison of ethanol and temperature tolerance of *Zymomonas mobilis* strain in glucose and molasses medium" *Indian Journal of Biotechnology*, Jan. 2007, pp. 74-77, vol. 6.

Ferain, T. et al. "Metabolic rerouting in a *Lactobacillus plantarum* strain deficient for lactate dehydrogenase" *Lait*, 1998, pp. 107-116, vol. 78.

(56) References Cited

OTHER PUBLICATIONS

All Press Releases, "Deinove, Young Innovative Enterprise specialized in biofuels, anchors its research in Montpelier" Oct. 15, 2008, pp. 1-8.
Chica, R.A., et al., "Semi-rational approaches to engineering enzyme activity: combining the benefits of directed evolution and rational design," *Current Opinion in Biotechnology*, 2005, vol. 16, No. 4, pp. 378-384.
Sen, S., etal., "Development in Directed Evolution for Improving Enzyme Functions," *Applied Biochemistry and Biotechnology*, 2007, vol. 143, No. 3, pp. 212-223.
Sanchez, A.M., "Efficient Succinic Acid Production from Glucose through Overexpression of Pyruvate Carboxylase in an *Escherichia coli* Alcohol Dehydrogenase and Lactate Dehydrogenase Mutant," *Biotechnology Progress*, 2005, vol. 21, No. 2, pp. 358-365.

\* cited by examiner

*D. radiodurans* R1 genome coordinates: 2362359 to 2362895 (SEQ ID NO: 1)

```
TTCCCCGCCTGGGTATCACGTCCCCGCCAGAGCCGCTCTGTACCTTCGGGGCATGACCCA
GCCCGTTTCTTCGGTTCCCGGCTCTTCCCTTTCCGGCGCAGGTTTTCAGCGACTGCTGGT
CGGGATCGATTTCTCGCCCTCGTCGTTGCACGCCCTTGAAGTGGCGCGGACCCGCTTTCC
CGGCGCGCGGCTGCGGCTCGCCCACGTGACCGACGCCCGCGCGGTGGCGGCTCCCGACGT
GGTGGGCGGCGTCACGCCGATCATGCCCGACCCGGGGCTGCTGCAAACGCTCGAAGACGC
CGATTCCAACCGGCTCTCGGGGCTGATCCGCGACGGTGAGGAAAGCGAGCTGCTCGTCGG
CGATCCCATCACGGGGCTGCTCGACGCGGCCCGGGCGTGGGCGCGGACCTGATCGTGGT
CGGCACCCACCCGCAGGGCGCGCTGGAACACTTTTTCATCGGCAGCAGCGCCGAGAAGCT
GGTGGGCCGCAGCGCGGTGCCGGTGCTGTGCGTGCCCTCGGGAGCACACAGATGAAA
```

*D. radiodurans* R1 genome coordinates: 2363484 to 2364098 (SEQ ID NO: 2)

```
TGGAACGAGCAGGTGCGCGCCAAAATCGATGAGGGCACCCGCAACGCCGCCGCCAGCATCATCGAGGG
CAAGCGGGCCACCTACTACGGCATCGGCGCGGCGCTCGCCCGCATCACCGAGGCCGTGCTGCGTGACC
GCCGCGCCGTCCTGACCGTCAGTGCGCCGACCCCCGAATACGGCGTGAGCCTCAGCCTGCCGCGTGTC
GTGGGCCGTCAGGGGGTGCTGTCCACCCTGCACCCCAAGCTGACCGGCGACGAGCAACAGAAGCTGGA
ACAGAGTGCCGGGGTGCTGCGCGGCTTCAAGCAGCAGCTCGGCCTGTGACGCCGACGCTCCAGACCGT
CTACGGCGAGGCGCAGCCGCTCGACTGGCTGTGCCTCGCCCCCACCCCGACGACGCCGAAATCGGCG
CGGGCGGCACGCTGATCCGGCTGGCGCAGGCGGGCCGGGCAGTGGGGATTCTGGAACTCACGCGCGGT
GAAAAGGGCACCCAGGGGACGCCCGCCGAGCGGCAGGCCGAGTGCGTGGCGGCGGCCCGCCTGATGGA
CCTGAGCTGGCGCGGCCAACTCGGGCTGCCCGATGGGGAACTCGCCGACACGCCGCCCTTTGCTCACG
CGT
```

Figure 2

Sequences of ZmPDC and ZmADH II

Zymomonas mobilis subsp. Mobilis ZM4 genome coordinates: 1375111 to 1373405
(SEQ ID NO: 3)

ATGAGTTATACTGTCGGTACCTATTTAGCGGAGCGGCTTGTCCAGATTGGTCTCAAGCATCACTTCGCAG

TCGCGGGCGACTACAACCTCGTCCTTCTTGACAACCTGCTTTTGAACAAAAACATGGAGCAGGTTTATTG

CTGTAACGAACTGAACTGCGGTTTCAGTGCAGAAGGTTATGCTCGTGCCAAAGGCGCAGCAGCAGCCGTC

GTTACCTACAGCGTCGGTGCGCTTTCCGCATTTGATGCTATCGGTGGCGCCTATGCAGAAAACCTTCCGG

TTATCCTGATCTCCGGTGCTCCGAACAACAATGATCACGCTGCTGGTCACGTGTTGCATCACGCTCTTGG

CAAAACCGACTATCACTATCAGTTGGAAATGGCCAAGAACATCACGGCCGCCGCTGAAGCGATTTACACC

CCGGAAGAAGCTCCGGCTAAAATCGATCACGTGATTAAAACTGCTCTTCGTGAGAAGAAGCCGGTTTATC

TCGAAATCGCTTGCAACATTGCTTCCATGCCCTGCGCCGCTCCTGGACCGGCAAGCGCATTGTTCAATGA

CGAAGCCAGCGACGAAGCTTCTTTGAATGCAGCGGTTGAAGAAACCCTGAAATTCATCGCCAACCGCGAC

AAAGTTGCCGTCCTCGTCGGCAGCAAGCTGCGCGCAGCTGGTGCTGAAGAAGCTGCTGTCAAATTTGCTG

ATGCTCTCGGTGGCGCAGTTGCTACCATGGCTGCTGCAAAAAGCTTCTTCCCAGAAGAAAACCCGCATTA

CATCGGCACCTCATGGGGTGAAGTCAGCTATCGGGCGTTGAAAAGACGATGAAAGAAGCCGATGCGGTT

ATCGCTCTGGCTCCTGTCTTCAACGACTACTCCACCACTGGTTGGACGGATATTCCTGATCCTAAGAAAC

TGGTTCTCGCTGAACCGCGTTCTGTCGTCGTTAACGGCATTCGCTTCCCCAGCGTCCATCTGAAAGACTA

TCTGACCCGTTTGGCTCAGAAAGTTTCCAAGAAAACCGGTGCATTGGACTTCTTCAAATCCCTCAATGCA

GGTGAACTGAAGAAAGCCGCTCCGGCTGATCCGAGTGCTCCGTTGGTCAACGCAGAAATCGCCCGTCAGG

TCGAAGCTCTTCTGACCCCGAACACGACGGTTATTGCTGAAACCGGTGACTCTTGGTTCAATGCTCAGCG

CATGAAGCTCCCGAACGGTGCTCGCGTTGAATATGAAATGCAGTGGGGTCACATTGGTTGGTCCGTTCCT

GCCGCCTTCGGTTATGCCGTCGGTGCTCCGGAACGTCGCAACATCCTCATGGTTGGTGATGGTTCCTTCC

AGCTGACGGCTCAGGAAGTCGCTCAGATGGTTCGCCTGAAACTGCCGGTTATCATCTTCTTGATCAATAA

CTATGGTTACACCATCGAAGTTATGATCCATGATGGTCCGTACAACAACATCAAGAACTGGGATTATGCC

GGTCTGATGGAAGTGTTCAACGGTAACGGTGGTTATGACAGCGGTGCTGGTAAAGGCCTGAAGGCTAAAA

CCGGTGGCGAACTGGCAGAAGCTATCAAGGTTGCTCTGGCAAACACCGACGGCCCAACCCTGATCGAATG

CTTCATCGGTCGTGAAGACTGCACTGAAGAATTGGTCAAATGGGGTAAGCGCGTTGCTGCCGCCAACAGC

CGTAAGCCTGTTAACAAGCTCCTCTAG

Figure 4

*Zymomonas mobilis subsp. Mobilis* ZM4 genome coordinates: 1634679 to 1635830
(SEQ ID NO: 4)

```
ATGGCTTCTTCAACTTTTTATATTCCTTTCGTCAACGAAATGGGCGAAGGTTCGCTTGAAAAAGCAATCA
AGGATCTTAACGGCAGCGGCTTTAAAAATGCGCTGATCGTTCTGATGCTTTCATGAACAAATCCGGTGT
TGTGAAGCAGGTTGCTGACCTGTTGAAAGCACAGGGTATTAATTCTGCTGTTTATGATGGCGTTATGCCG
AACCCGACTGTTACCGCAGTTCTGGAAGGCCTTAAGATCCTGAAGGATAACAATTCAGACTTCGTCATCT
CCCTCGGTGGTGGTTCTCCCCATGACTGCGCCAAAGCCATCGCTCTGGTCGCAACCAATGGTGGTGAAGT
CAAAGACTACGAAGGTATCGACAAATCTAAGAAACCTGCCCTGCCTTTGATGTCAATCAACACGACGGCT
GGTACGGCTTCTGAAATGACGCGTTTCTGCATCATCACTGATGAAGTCCGTCACGTTAAGATGGCCATTG
TTGACCGTCACGTTACCCCGATGGTTTCCGTCAACGATCCTCTGTTGATGGTTGGTATGCCAAAAGGCCT
GACCGCCGCCACCGGTATGGATGCTCTGACCCACGCATTTGAAGCTTATTCTTCAACGGCAGCTACTCCG
ATCACCGATGCTTGCGCTTTGAAAGCAGCTTCCATGATCGCTAAGAATCTGAAGACCGCTTGCGACAACG
GTAAGGATATGCCGGCTCGTGAAGCTATGGCTTATGCCCAATTCCTCGCTGGTATGGCCTTCAACAACGC
TTCGCTTGGTTATGTCCATGCTATGGCTCACCAGTTGGGCGGTTACTACAACCTGCCGCATGGTGTCTGC
AACGCTGTTCTGCTTCCGCATGTTCTGGCTTATAACGCCTCTGTCGTTGCTGGTCGTCTGAAAGACGTTG
GTGTTGCTATGGGTCTCGATATCGCCAATCTCGGTGATAAAGAAGGCGCAGAAGCCACCATTCAGGCTGT
TCGCGATCTGGCTGCTTCCATTGGTATTCCAGCAAACCTGACCGAGCTGGGTGCTAAGAAAGAAGATGTG
CCGCTTCTTGCTGACCACGCTCTGAAAGATGCTTGTGCTCTGACCAACCCGCGTCAGGGTGATCAGAAAG
AAGTTGAAGAACTCTTCCTGAGCGCTTTCTAA
```

Figure 4 (continued)

RECOMBINANT BACTERIA AND THE USES THEREOF FOR PRODUCING ETHANOL

CROSS-REFERENCE TO RELATED APPLICATIONS

This application is a continuation of U.S. application Ser. No. 13/319,526, filed Nov. 9, 2011, now U.S. Pat. No. 9,034,619, which is the U.S. national stage application of International Patent Application No. PCT/EP2010/056592, filed May 12, 2010.

The Sequence Listing for this application is labeled "Seq-List.txt" which was created on Oct. 27, 2011 and is 7 KB. The entire contents of the sequence listing is incorporated herein by reference in its entirety.

The present invention relates to recombinant bacteria and the uses thereof, particularly for the production of ethanol. The invention also relates to methods for the production of such bacteria, as well as to nucleic acid constructs suitable for such production. The invention specifically relates to bacteria lacking a functional LDH gene and/or containing a recombinant nucleic acid encoding a PDC or ADH. The bacteria of this invention may be produced from any stress-resistant bacteria, particularly from any strain of *Deinococcus*, including extremophile strains, such as, without limitation, *D. radiodurans, D. geothermalis, D. murrayi, D. cellulosilyticus* or *D. deserti*.

INTRODUCTION

Bacteria having the capacity to reassemble their genome when disrupted by a stress have been reported in the literature, such as *Deinococcus* bacteria. *Deinococcus* is a gram positive bacterium that was isolated in 1956 by Anderson and collaborators. This extremophile organism is resistant to DNA damage by UV and ionizing radiations or by cross-linking agent (mitomycin C) and is tolerant to desiccation.

WO01/023526 shows the unusual resistance of *Deinococcus* to radiation and further proposes their engineering and use in bioremediation. Patent application No. WO2009/063079, unpublished at the priority date of the present application, shows that *Deinococcus* bacteria can resist to solvents and transform biomass to generate ethanol.

Other stress-resistant bacteria are disclosed in patent application No. EP09 305041.7, presently unpublished, as well as methods for their isolation and/or selection, and their ability to produce metabolites such as antibiotics.

Genetically altered gram-positive or *Geobacillus* strains have been mentioned in WO95/27064 and WO2006/131734. From the industrial perspective, no satisfactory metabolite production has been disclosed for these strains. Furthermore, *Geobacillus* strains produce spores, which is a substantial drawback for industrial use.

The present invention now shows that the genome of stress-resistant bacteria, particularly *Deinococcus* bacteria, can be modified to improve their capacity to produce ethanol. More specifically, the present invention shows that it is possible to modify metabolic pathways within stress-resistant bacteria, particularly *Deinococcus* bacteria in order to increase their performance in the production of ethanol.

SUMMARY OF THE INVENTION

An object of this invention relates to a recombinant stress-resistant bacterium, particularly *Deinococcus* bacterium, wherein said bacterium has a modified genome containing an inactive L-lactate dehydrogenase (LDH) gene.

In a particular embodiment, the LDH gene is deleted, in all or in part, and does not encode a functional lactate dehydrogenase enzyme.

The recombinant bacterium of this invention preferably further comprises a recombinant nucleic acid molecule encoding a pyruvate decarboxylase (PDC) and/or an alcohol dehydrogenase (ADH).

In this regard, a further object of this invention is a recombinant stress-resistant bacterium, particularly *Deinococcus* bacterium, wherein said bacterium contains a recombinant nucleic acid, preferably a plasmid, containing a nucleic acid encoding a pyruvate decarboxylase and/or an alcohol dehydrogenase.

The bacterium of the invention may be selected from various species of stress-resistant bacteria, such as *Deinococcus* bacteria, *Tepidimonas* bacteria, *Truepera* bacteria, *Porphyrabacter* bacteria, *Novosphingobium* bacteria or *Exiguobacterium* bacteria. Preferred bacteria of this invention are *Deinococcus* bacteria such as, without limitation, *D. radiodurans, D. geothermalis, D. murrayi, D. cellulosilyticus* or *D. deserti*, preferably a thermophilic *Deinococcus* bacterium.

A further object of this invention resides in a method of producing a biofuel, particularly ethanol, comprising cultivating a bacterium as defined above in the presence of an appropriate substrate, and collecting the biofuel.

The invention also relates to the use of a bacterium as defined above for producing ethanol.

The invention also relates to a method for producing a recombinant stress-resistant bacterium, particularly *Deinococcus* bacterium, as defined above, or an ancestor thereof, the method comprising:
providing a (parent) stress-resistant bacterium, particularly *Deinococcus* bacterium;
Treating the bacterium to inactivate the LDH gene, and
Selecting a bacterium having an inactivated LDH gene.

The invention also relates to a method for producing a recombinant stress-resistant bacterium, particularly *Deinococcus* bacterium, as defined above, or an ancestor thereof, the method comprising:
providing a (parent) stress-resistant bacterium, particularly *Deinococcus* bacterium;
introducing into said bacterium a recombinant nucleic acid molecule encoding a PDC and/or an ADH, and
Selecting a bacterium which expresses said nucleic acid.

The invention also relates to a plasmid construct, wherein said plasmid replicates in a *Deinococcus* bacterium and contains a nucleic acid encoding a PDC and/or an ADH.

LEGEND TO THE FIGURES

The patent or application file contains at least one drawing executed in color. Copies of this patent or patent application publication, with color drawing(s), will be provided by the Office upon request and payment of the necessary fee.

FIG. 1: Construction and structure of the integrative construct pDR-LDHdel for partial LDH deletion. The insert with homologous regions and chloramphenicol cassette was synthesized and cloned in LITMUS28i. $Cam^R$, chloramphenicol resistance; $Amp^R$, ampicilline resistance; GDR_term85, putative *Deinococcus radiodurans* transcription terminator; P D. rad., *Deinococcus radiodurans* putative promoter; 5'HR, 5' homologous region; 3'HR, 3' homologous region; E. coli ORI, *Escherichia coli* replication origin.

FIG. 2: Sequences of 5' (SEQ ID NO: 1) and 3' (SEQ ID NO: 2) homologous regions.

Figure 3:
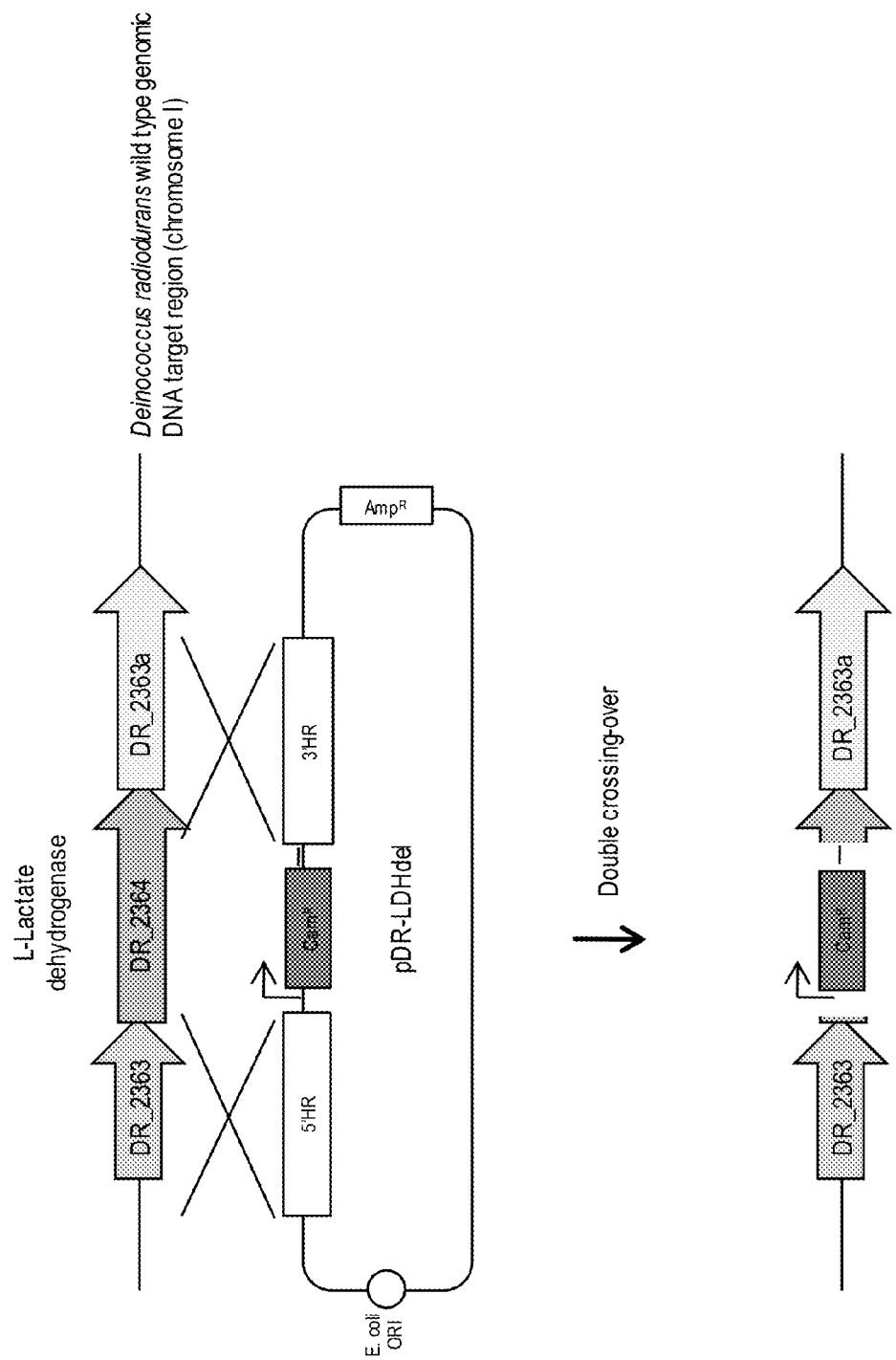
Figures 5A, 5B:
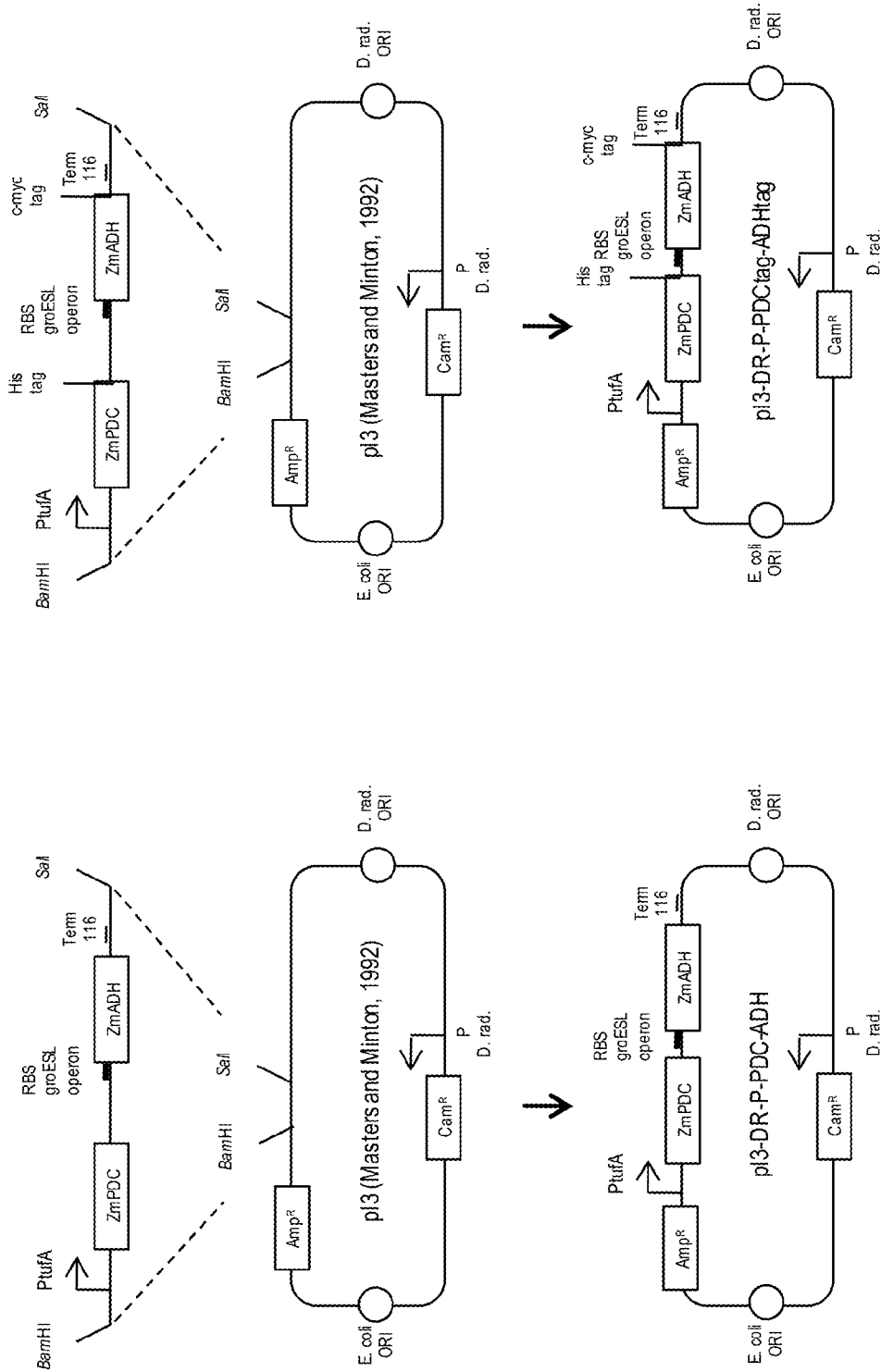
Figures 5C, 5D:
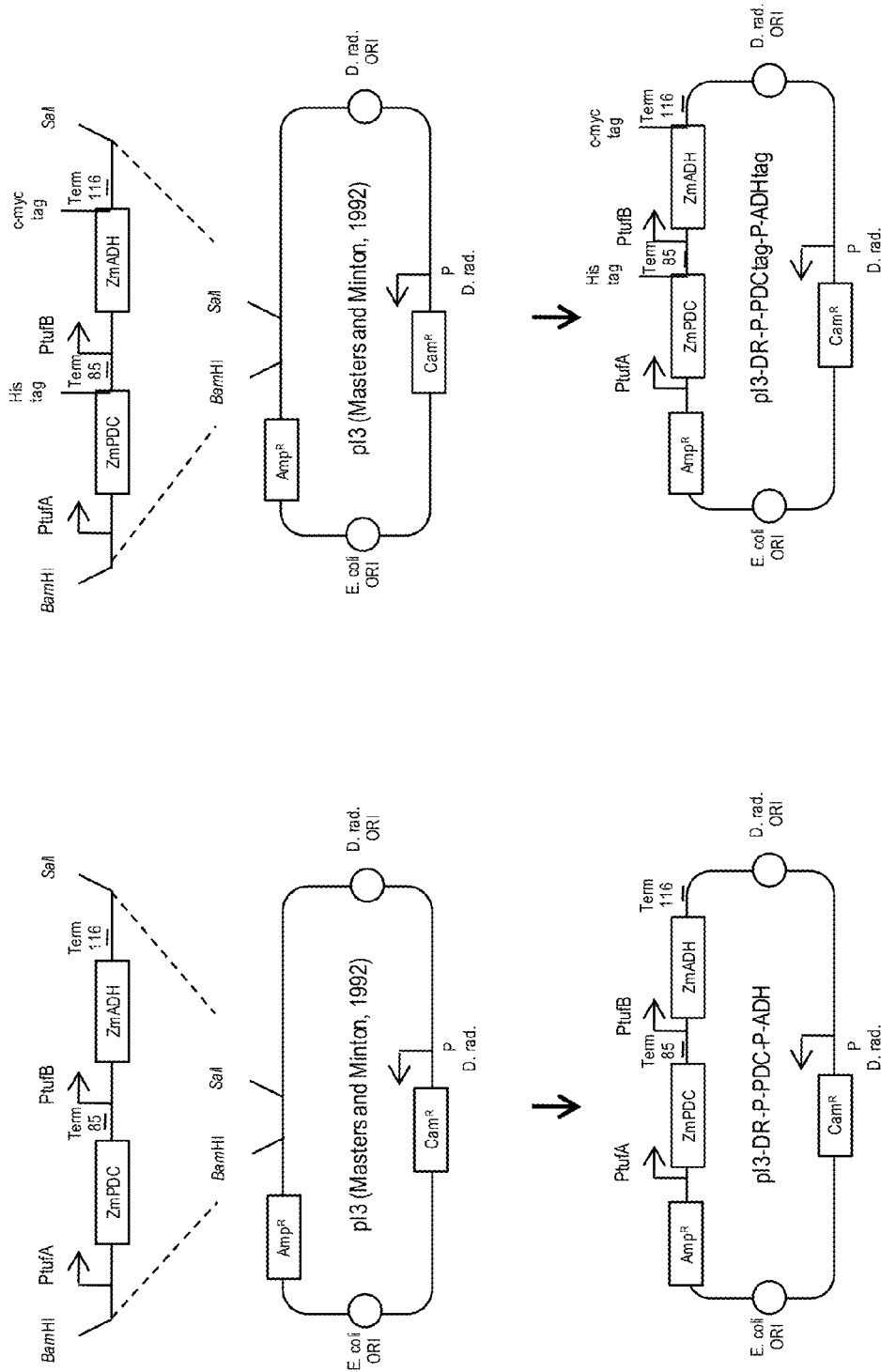

FIG. 3: Process of construction of L-lactate dehydrogenase (locus DR_2364) *Deinococcus radiodurans* mutants by homologous recombination. Cam$^R$, chloramphenicol resistance; Amp$^R$, ampicilline resistance; 5'HR, 5' homologous region; 3'HR, 3' homologous region; *E. coli* ORI, *Escherichia coli* replication origin.

FIG. 4: Nucleic acid sequences of ZmPDC (SEQ ID NO: 3) and ZmADH II (SEQ ID NO: 4) genes.

FIGS. 5a-5d: Construction and structure of plasmids pI3-DR-P-PDC-ADH (a), pI3-DR-P-PDCtag-ADHtag (b), pI3-DR-P-PDC-P-ADH (c) and pI3-DR-P-PDCtag-P-ADHtag (d). RBS groESL operon, ribosomal binding site region located upstream of *Deinococcus radiodurans* groESL operon (Meima et al, 2001); Amp$^R$, ampicilline resistance; Cam$^R$, chloramphenicol resistance; *E. coli* ORI, *Escherichia coli* replication origin; PtufA, 432 bp located upstream of the predicted translational start codon of tufA gene; PtufB, 234 bp located upstream of the predicted translational start codon of tufB gene; ZmPDC, *Zymomonas mobilis* pyruvate decarboxylase gene; ZmADH, *Zymomonas mobilis* alcohol dehydrogenase II gene; Term85, intergenic sequence located between locus DR_1184 and DR_1185 containing a putative transcription terminator; Term116, transcription terminator Term116 (Lecointe et al, 2004); D. rad. ORI, *Deinococcus radiodurans* replicative origin; P D. rad., *Deinococcus radiodurans* promoter.

Figure 6A:
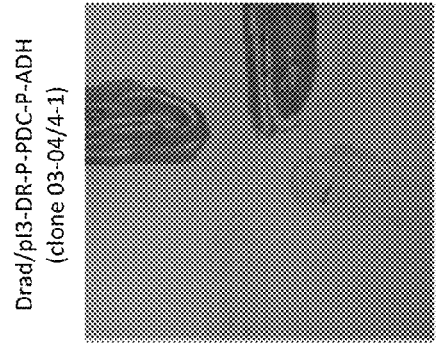
Figure 6B:
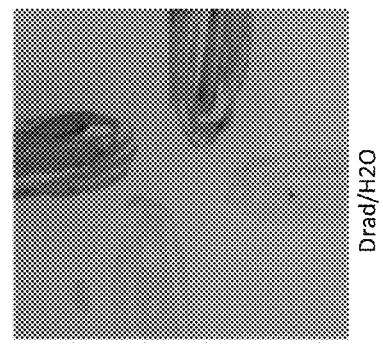

FIGS. 6a-6b: Alcohol dehydrogenase activity for *D. radiodurans* transformed with pI3-DR-P-PDC-P-ADH (a) or pI3-DR-P-PDCtag-P-ADHtag (b).

Figure 7:
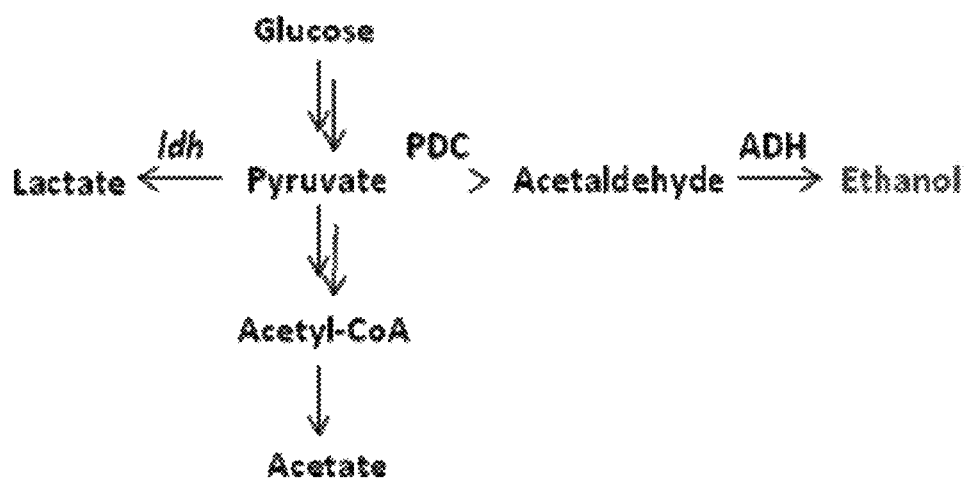

FIG. 7: Re-engineered metabolic pathway.

Figure 8:
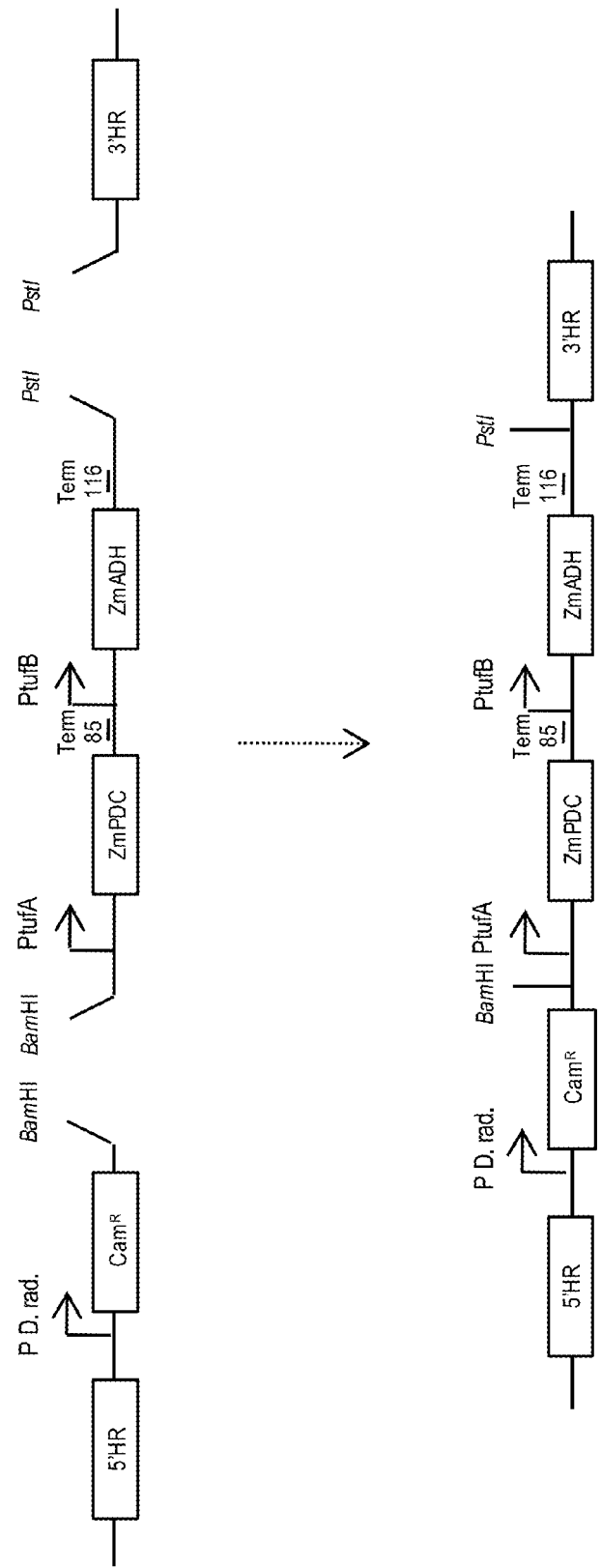

FIG. 8: Tripartite ligation of PCR products for the creation of the PDC+ADH+LDH− mutant. Cam$^R$, chloramphenicol resistance; PtufA, 432 bp located upstream of the predicted translational start codon of TufA gene; PtufB, 234 bp located upstream of the predicted translational start codon of TufB gene; ZmPDC, *Zymomonas mobilis* pyruvate decarboxylase gene; ZmADH, *Zymomonas mobilis* alcohol dehydrogenase II gene; Term85, intergenic sequence located between locus DR_1184 and DR_1185 containing a putative transcription terminator; Term116, transcription terminator Term116 (Lecointe et al, 2004); P D. rad., *Deinococcus radiodurans* putative promoter; 5'HR, 5' homologous region; 3'HR, 3' homologous region.

Table 1: Name of recombinants used for metabolic analysis.

Tables 2-5: *Deinococcus* recombinants: Metabolites production in Complex or Defined medium.

DETAILED DESCRIPTION OF THE INVENTION

The present invention relates to recombinant stress-resistant bacteria and the uses thereof for producing a biofuel or other metabolites.

Within the context of this invention, the term "stress-resistant bacterium" designates more specifically a bacterium having the capacity to reassemble its genome, in full or in part, when disrupted by a stress. The stress may be any cell-destructing DNA damaging treatment, i.e., a treatment that is sufficient to cause 90% cell death, or more, in a culture of *E. coli* bacteria. Even more preferably, the cell-destructing DNA damaging treatment is a treatment that is sufficient to reduce by at least 2 log the bacterial titer in a culture of *E. coli*. Examples of such treatment include irradiation, preferably repeated and sequential UV irradiation, and/or the use of genotoxic agents. A preferred stress treatment is a UV treatment of between 0.5 and 400 mJ/cm2, more preferably of between 1 and 200 mJ/cm2, typically between 1 and 100 mJ/cm2, applied for a period of time of about 5" to 5'. A preferred UV treatment is 4 mJ/cm2 for 30 seconds, which may be repeated at an interval of between 1 and 8 hours, preferably 3 to 5 hours, and more preferably of about 4 hours. Specific cell stress treatments according to the invention have been described in patent application No. EP09 305041.7, unpublished, which is incorporated therein by reference.

Cell-stress resistant bacteria according to the present invention include more specifically *Deinococcus* bacteria, *Tepidimonas* bacteria, *Truepera* bacteria, *Porphyrabacter* bacteria, *Novosphingobium* bacteria or *Exiguobacterium* bacteria. Preferred bacteria of this invention are *Deinococcus* bacteria, particularly extremophile *Deinococcus* bacteria, more preferably *Deinococcus* bacteria selected from *D. radiodurans, D. geothermalis, D. murrayi, D. cellulosilyticus* or *D. deserti*, preferably a thermophilic *Deinococcus* bacterium.

*Deinococcus* bacteria have been shown to have the capacity to reassemble their genome, in full or in part, when disrupted by a stress. As previously mentioned, these bacteria, particularly *D. radiodurans*, have been proposed for bioremediation. The ability of *Deinococcus* bacteria to produce bioenergy products from biomass is disclosed in WO2009/063079, unpublished at the priority date of the present application. The present invention now shows that the performance of stress-resistant bacteria such as *Deinococcus* bacteria can be improved by re-engineering metabolic pathways using recombinant technologies. More particularly, the invention provides novel recombinant stress-resistant bacteria having a re-engineered ethanol biosynthesis pathway.

In this respect, the inventors have designed and created novel biosynthetic pathways into stress-resistant bacterial strains, which are based on a re-routing of the pyruvate conversion pathway. More particularly, the inventors have designed new recombinant strains in which pyruvate is efficiently used as a substrate to produce ethanol. In this respect, the inventors have inserted one or several enzymes (or corresponding genes) which cause or catalyse the conversion of pyruvate into ethanol. The inventors have also deleted an endogenous pathway which uses pyruvate to produce lactate, thereby increasing the amounts of pyruvate engaged in the ethanol synthetic pathway.

An object of this invention thus relates to a (recombinant or genetically modified) stress-resistant bacterium, particularly *Deinococcus* bacterium, wherein said bacterium contains a recombinant nucleic acid encoding a PDC.

The term "recombinant bacterium" designates a bacterium which contains a modified genome as a result of either a deletion and/or insertion of a heterologous (e.g., not naturally present in said bacterium) nucleic acid sequence or molecule. A "recombinant nucleic acid" therefore designates a nucleic acid which has been engineered and is not found as such in wild type bacteria.

Another object of this invention relates to a (recombinant or genetically modified) stress-resistant bacterium, particularly *Deinococcus* bacterium, wherein said bacterium contains a recombinant nucleic acid encoding an ADH.

In a further preferred embodiment, the invention relates to a (recombinant or genetically modified) stress-resistant bacterium, particularly *Deinococcus* bacterium, wherein said bacterium contains a recombinant nucleic acid encoding a PDC and an ADH.

Another object of this invention relates to a (recombinant or genetically modified) stress-resistant bacterium, particularly *Deinococcus* bacterium, wherein said bacterium has a modified genome containing an inactive lactate dehydrogenase (LDH) gene.

A most preferred object of this invention is a (recombinant or genetically modified) stress-resistant bacterium, particularly *Deinococcus* bacterium, wherein said bacterium has a modified genome containing an inactive lactate dehydrogenase (LDH) gene and further wherein said bacterium contains a recombinant nucleic acid encoding a PDC and/or an ADH.

Pyruvate decarboxylase (PDC, EC: 4.1.1.1) catalyses the mono-oxidative decarboxylation of pyruvate to acetaldehyde and carbon dioxide. Alcohol dehydrogenase (ADH, EC: 1.1.1.1) catalyses the conversion of acetaldehyde to ethanol.

In order to create or improve this metabolic pathway, a nucleic acid molecule encoding a PDC and/or an ADH has been cloned and successfully introduced into a stress-resistant bacterium, particularly a *Deinococcus* strain. The term nucleic acid designates preferably DNA, although the recombinant nucleic acid may be RNA. Depending on the situation, the nucleic acid molecule may be double- or single-stranded.

More particularly, a nucleic acid molecule encoding a functional PDC has been prepared. Such a nucleic acid molecule can comprise all or a portion of the sequence of a natural or synthetic or mutant PDC gene, as long as the nucleic acid molecule encodes a protein that catalyses the mono-oxidative decarboxylation of pyruvate to acetaldehyde and carbon dioxide.

PDC is present in plants, fungi and yeast but is rare in bacteria. No apparent PDC has been found in *D. radiodurans* genome that was fully sequenced. PDC genes have been identified in various strains, such as in *Zymomonas mobilis* (Brau and Sahm, 1986; Conway et al, 1987a; Neale et al, 1987), in *Acetobacter pasteurianus* (Genbank: AF368435) (Chandra et al, 2001), in *Sarcina ventriculi* (Genbank: AF354297) (Lowe and Zeikus, 1992) and in *Zymobacter palmae* (Genbank: AF474145) (Raj et al, 2002).

In a preferred embodiment, the PDC nucleic acid comprises the sequence of all or part of a bacterial PDC gene. In a specific embodiment, the nucleic acid comprises the sequence of a PDC gene from *Zymomonas mobilis* (ZmPDC, ZMO1360). ZmPDC gene sequence comprises 1707 base pairs and is represented FIG. 4.

Furthermore, in order to create an ADH activity in stress-resistant bacteria such as *Deinococcus*, a nucleic acid molecule encoding a functional ADH has been prepared. Such a molecule can comprise all or a portion of the sequence of a natural or synthetic or mutant ADH gene, as long as the nucleic acid molecule encodes a protein that catalyses the conversion of acetaldehyde to ethanol.

ADH genes have been cloned from different organisms including, without limitation, *Zymomonas mobilis* (Ingram et al, 1987), *Lactobacillus brevis* (Liu et al, 2007), or *Geobacillus stearothermophilus* (Genbank: Z25544) (Talarico et al, 2005). A putative ADH gene (DR_2279) has also been found in *D. radiodurans* genome. However, the expression thereof, alone, does not seem to allow efficient production of ethanol.

In a preferred embodiment, the ADH nucleic acid comprises the sequence of all or part of a bacterial ADH gene. In a specific embodiment, the nucleic acid comprises the sequence of an ADH gene from *Zymomonas mobilis* (ZmADH, ZMO1596). ZmADH II comprises 1152 base pairs and the sequence thereof is depicted FIG. 4.

These nucleic acids may further contain regulatory sequences or regions, such as a promoter (e.g., a tufB promoter) and a terminator, for instance. The promoter may be endogenous to the host (e.g, a promoter from a *Deinococcus* gene for cloning a recombinant nucleic acid of the invention in a *Deinococcus* strain) or heterologous (e.g., from a distinct origin, such as a distinct bacterium, a phage, a synthetic or hybrid promoter, etc.). Preferred promoters are endogenous. In this regard, *Deinococcus* promoters have been studied and used for gene expression. Examples of such promoters include PtufA and PtufB from the translation elongation factors Tu genes tufA (DR0309) and tufB (DR2050), the promoter of the resU gene encoding a putative resolvase located in pI3, and the promoter region PgroESL of the groESL operon (Lecointe et al, 2004; Meima et al, 2001).

The nucleic acids may be cloned as separate entities (e.g., distinct nucleic acid constructs), or in a same construct, under distinct promoter regions or in operon.

The examples provided in the present application disclose the creation of new constructs where a ZmPDC gene and an alcohol dehydrogenase II gene from *Zymomonas mobilis* (ZmADH) were cloned in the same construct, either under separate promoters or in operon. These constructs were successfully introduced into *Deinococcus* strains, which resulted in ethanol production from said recombinant strains while the unmodified (parent) strain did not produce any ethanol under the tested conditions.

The nucleic acid(s) may be inserted into the genome of the bacterium, or inserted as (autonomously) replicating molecules, e.g., on a plasmid, episome, artificial chromosome, etc.

In a typical embodiment, the recombinant nucleic acid(s) is/are cloned into a suitable vector, which may be replicative in *Deinococcus*. Typical plasmids contain, in addition to the cloned insert, a selection gene (e.g., antibiotic resistance, a dye, etc.) and an origin of replication effective in *Deinococcus* or allowing integration into the genome of *Deinococcus*. The plasmid (or the recombinant nucleic acids) may further comprise regulatory sequences, such as for instance promoters, terminators and/or enhancers.

Examples of such vectors include pMD66, pI3, pRAD1 and pUE30. pMD66 is a large vector (27 kb) for *D. radiodurans* and *E. coli* containing a 12 kb fragment of pI3 (Daly et al, 1994). pI3 was described by Masters and Minton (1992). pRAD1 is a *D. radiodurans-E. coli* shuttle plasmid containing a minimal replicon for *D. radiodurans* (Meima and Lidstrom, 2000). pUE30 is an endogenous plasmid derived from a strain of *D. radiopugnans* which is able to replicate in *Deinococcus* (see US2003/0175977).

A particular object of this invention resides in a plasmid construct, wherein said plasmid replicates in a stress-resistant bacterium, particularly a *Deinococcus* bacterium, and contains a nucleic acid encoding a PDC and/or an ADH. The PDC and ADH coding nucleic acids may be in operon or as distinct expression units in the same plasmid or in distinct plasmids. Preferred plasmids of this invention encode a PDC and/or an ADH from *Zymomonas*. Specific examples of plasmids of this invention are pI3-DR-P-PDC-ADH, pI3-DR-P-PDCtag-ADHtag, pI3-P-PDC-P-ADH and pI3-DR-P-PDCtag-P-ADHtag.

The recombinant nucleic acid may also be cloned into an integrative cassette suitable for integration into the genome of a *Deinococcus* bacterium. Such an integrative cassette comprises, typically, the recombinant nucleic acid linked to (or flanked by) one or several sequences allowing integration, preferably site-specific integration. Such sequences may be for instance nucleic acid sequences homologous to a targeted region of the genome, allowing integration through crossing over. In this regard, a particular bacterium of the invention comprises a recombinant nucleic acid encoding a PDC and/or an ADH integrated into its genome, in replacement of all or part of the endogenous gene encoding LDH. In this context, the term "part of the LDH gene" means any portion of the gene the deletion of which being sufficient to cause inactivation of the gene in the cell.

Various techniques can be used to insert a recombinant nucleic acid molecule(s) into stress-resistant bacteria, particularly Deinococcus. In particular, they may be inserted through natural transformation (which can be further enhanced in presence of calcium chloride) or electroporation.

In this respect, the invention also relates to a method for producing a recombinant stress-resistant bacterium, particularly a Deinococcus bacterium as defined above, or an ancestor thereof, the method comprising:

providing a (parent) stress-resistant bacterium, particularly a Deinococcus bacterium;

introducing into said bacterium a recombinant nucleic acid molecule encoding a PDC and/or an ADH, and Selecting a bacterium which expresses said nucleic acid.

Recombinants having inserted the nucleic acids may be selected according to techniques known per se, such as antibiotic resistance.

Expression of appropriate PDC or ADH may be verified using quantitative PCR and production of these enzymes may be verified by Western blot or by enzymatic assays known per se in the art. PDC activity can be measured by analyzing the reduction of $NAD^+$ and ADH activity can be measured by analyzing the reduction of $NAD^+$ or oxidation of NADH due to the activity of these enzymes (Conway et al, 1987a and b).

As disclosed in the experimental section, Deinococcus bacteria containing a recombinant nucleic acid encoding a PDC and ADH have been produced. These bacteria can be cultivated, are viable and stably contain the recombinant nucleic acid. Stability of the recombinants is preferably such that more than 95% of the transformed bacteria still contain the vector after 2 growth cycles. The results show that PDC and ADH genomic insertion is stable even after 2 growth cycles.

These bacteria produce ethanol and combine many advantages in terms of substrate specificity, culture conditions and metabolite production.

Furthermore, in order to further improve ethanol production, stress-resistant bacteria, particularly Deinococcus bacteria in which the lactate dehydrogenase gene is rendered inactive have also been produced.

The LDH (lactate dehydrogenase) gene is involved in the conversion of pyruvate into lactate. D. radiodurans LDH gene was cloned in 1996 by Narumi and Watanabe. This enzyme is tetrameric and its crystallographic structure was solved (Coquelle et al, 2007).

The inventors have now created a novel bacterium in which said enzyme is inactive. In a particular embodiment, the LDH gene is deleted, in all or in part, and does not encode a functional protein. The LDH gene may be inactivated in said bacterium or an ancestor thereof, by homologous recombination, gene replacement, or targeted mutagenesis, or any other technique known per se in the art.

In a preferred embodiment, the LDH gene is inactivated by deletion of at least part of said gene, which may be replaced by heterologous nucleic acid (e.g., a selection marker).

The LDH gene contains 915 base pairs. It is located between the coordinates 2362890 and 2363804 in the genome of Deinococcus. The sequence of said gene is available e.g., under geneSeq1799712. In a preferred embodiment, the bacterium of the present invention lacks a portion of said gene, preferably at least 100 consecutive nucleotides thereof, more preferably at least 200, 300, 400 or 500. In the examples, a defective Deinococcus strain has been produced, which lacks 589 consecutive nucleotides of the LDH gene. This strain has been prepared by double crossing-over using a particular construct comprising a marker gene flanked by two regions homologous to portions of the LDH gene and (optionally) to portions of regions flanking the LDH gene (see FIG. 3). Typical homologous regions should be long enough to allow hybridization and crossing-over, e.g., above 200 nucleotides, preferably above 300 nucleotides, typically between 300 and 700. Such constructs represent particular object of the present invention (see FIGS. 1 and 2).

In this regard, the invention also relates to a method for producing a recombinant stress-resistant bacterium, particularly a Deinococcus bacterium as defined above, or an ancestor thereof, the method comprising:

providing a (parent) stress-resistant bacterium, particularly a Deinococcus bacterium;

Treating the bacterium to inactivate the LDH gene, and

Selecting a bacterium having an inactivated LDH gene.

The bacterium of the present invention may be cultivated and/or maintained in any suitable culture medium and device. Examples of such medium include complex glucose medium or defined medium as disclosed in the examples, such as e.g., defined medium sucrose, defined medium starch. Suitable medium are also commercially available.

A further of object of the present invention relates to the use of a bacterium as defined above for producing ethanol or other metabolites.

The invention also relates to a method of producing a biofuel, particularly ethanol, comprising cultivating a bacterium as defined above in the presence of an appropriate substrate, and collecting the biofuel.

The substrate may be any culture medium or various types of biomass or products derived therefrom. In particular, the biofuel may be produced from renewable resources, especially plant or animal biomass, or from municipal and industrial wastes.

The term biofuel according to the invention comprises "first generation biofuel" and/or "second generation biofuel". First generation biofuels are obtained from vegetal or animal organic material, preferably from sugar, starch, vegetable oil or animal fats. The main source for the production of first generation biofuels are edible plants or parts thereof. The first generation biofuels include vegetable oil, biodiesel, bioalcohols, biogas, syngas and solid biofuels. Bioalcohols include ethanol, propanol and butanol. The second generation biofuels are produced preferably from non-edible plants or non-edible parts of plants. They include non-food crops, biomass wastes, stalks of wheat, corn and wood.

More preferably, the method of the invention is used for the production of ethanol.

The method of the invention may be performed in a reactor of conversion. By "reactor" is meant a conventional fermentation tank or any apparatus or system for biomass conversion specially designed to implement the invention and therefore consisting in particular of bioreactors, biofilters, rotary biological contactors, and other gaseous and/or liquid phase bioreactors, especially those adapted for the treatment of biomass or biomass derivatives. The apparatus which can be used according to the invention can be used continuously or in batch loads.

In the reactor, to implement the method of the invention, at least one bacterium of the invention, or bacterial extract thereof, is used, whilst said reactor is arranged and supplied so that physicochemical conditions are set up and maintained therein so that said bacterium is operational for the application under consideration and so that, optionally, bacterial growth is possible and preferably promoted therein.

The process may be conducted under aerobiosis, anaerobiosis or under microaerobiosis, depending on the substrate and bacterium. An advantage of the invention relates in the ability of the bacteria of the invention to resist stressful conditions, including the presence of ethanol in the culture medium. The process of the invention may thus preferably be performed at a temperature of about 40° C. or more, particularly a temperature comprised between 40-70° C.; under acid pH conditions, and/or in the presence of ethanol.

Further aspects and advantages of the invention will be disclosed in the following examples, which should be considered as illustrative and do not limit the scope of this application.

Examples

Materials and Methods
Bacterial Strains and Growth Conditions:

*Escherichia coli* (*E. coli*) strains SCS110, JM109 or DH5α were used to propagate plasmids. They were cultivated at 37° C. and 200 RPM in Luria-Bertani (LB) Broth (per liter: Tryptone 10 g, Yeast extract 5 g, Sodium chloride 10 g). Solid media was prepared by addition of Agar 1.5%.

*Deinococcus radiodurans* R1 (*D. radiodurans*) was cultivated at 30° C. and 200 RPM in TGY or PGY. The composition of the TGY medium is the following, per liter: Tryptone (5 g), Yeast extract (1.5 g) and Glucose (1 g). Composition of the solid media is, per liter: Tryptone (5 g), Yeast extract (2.5 g), Glucose (1 g) and Agar (15 g). The composition of the PGY medium is the following, per liter: Peptone (10 g), Yeast extract (5 g) and Glucose (1 g). Composition of the solid media is, per liter: Peptone (10 g), Yeast extract (5 g), Glucose (1 g) and Agar (15 g).

LB or TGY media were supplemented, if necessary, with appropriate antibiotics (chloramphenicol at a final concentration of 3 µg/ml for *D. radiodurans* transformants and ampicilline 100 µg/ml for *E. coli* transformants).

Transformation:

*E. coli* transformation was done using commercial competent cells SCS110 from Stratagene or JM109 from Promega.

For *D. radiodurans* competent cells preparation, a fresh culture in stationary phase was diluted 100 times in 50 ml of TGY. Cells were grown until early exponential phase ($OD_{600\,nm}$=0.3); the pellet was resuspended in an appropriate volume of ice cold 2×TGY/10% v/v Glycerol/30 mM $CaCl_2$. For transformation, desired amount of plasmid DNA was added to 100 µl of the cells. The mixture was incubated 30 minutes on ice before the tubes were transferred at 30° C. After 90 minutes of incubation at 30° C., 900 µl of prewarmed 2×TGY was added to the cells. The transformants were shaken at 200 RPM and 30° C. during 20 hours. They were serially diluted and spread on appropriate non selective or selective TGY plates.

DNA Manipulation:

LITMUS28i is from New England Biolabs.

Plasmid minipreparation from *E. coli* cells was done using the kit Wizard®Plus SV minipreps DNA purification system from Promega and midipreparation was done using the Plasmid DNA purification NucleoBond® Xtra Midi Plus EF kit from Macherey-Nagel. These preparations were done from 3-100 ml of *E. coli* culture in stationary phase.

For plasmid preparation from *D. radiodurans*, 50 ml of cells in stationary phase were resuspended in 0.5M EDTA and 0.5M EDTA saturated butanol. After 15 minutes incubation at room temperature, the pellet was resuspended in 0.5M EDTA and the cells were placed at 70° C. during 30 minutes. The pellet was washed twice in lysozyme buffer (10 mM Tris HCl, 5 mM EDTA, 0.5M NaCl) before addition of lysozyme at 5 mg/ml (in lysozyme buffer). The sample was incubated for 30 minutes at 37° C. before the addition of RNAse and proteinase K. The mix was incubated during 1 hour at 56° C. 200 mM NaOH was then added to the sample which was inverted several times to mix; 3M potassium acetate was added to the sample which was inverted to mix; the mixture was incubated for 10 minutes on ice before ethanol was added to the supernatant; this mixture was incubated for 10 minutes on ice and the pellet is washed with ethanol 70%. The dried DNA pellet was resuspended in water.

Genomic DNA extraction from *D. radiodurans* was done using the DNeasy® Blood and Tissue commercial kit from Qiagen. These preparations were done from 5 ml of stationary phase cultures.

The oligonucleotides were synthesized by Eurogentec. The polymerases used for PCR amplification were the DyNAzyme EXT DNA polymerase from Finnzymes or the Extensor Hi-Fidelity PCR Enzyme from Thermo Scientific. PCR fragments were cleaned up using the Wizard SV Gel and PCR Clean-Up System kit from Promega.

The T4 DNA ligase (New England Biolabs) was used for DNA ligation.

Plasmidic DNA or PCR products were digested with restriction enzymes coming from New England Biolabs.

Genetic material (PCR or digestion products) were separated by agarose gel electrophoresis. DNA was quantified with a Biophotometer from Eppendorf.

DNA inserts were synthetized by Genecust Europe and cloned into an appropriate vector.

Alcohol Dehydrogenase Activity Test:

4 ml of pararosaniline (Sigma) at 2.5 mg/ml in absolute ethanol were added to 200 ml of LB agar containing 50 mg of sodium bisulfite (Conway et al, 1987b). 2-days-old *D. radiodurans* cells grown on TGY agar plates (supplemented if necessary with the appropriate antibiotic) were plated on the indicator plates and incubated at 37° C. for 2 to 3 hours.

Metabolites Production:

This method enables the evaluation of the ability of genetically modified micro-organisms to produce metabolites of interest from biomass or a derivative of biomass.

The test is carried out at 30° C.

From pre-cultures (in stationary phase) prepared in Complex medium Glucose, 6 ml of enriched medium are seeded (seeding at 1% v/v).

The enriched culture mediums tested are Complex Medium Glucose, Defined Medium Sucrose, Defined Medium Starch.

Complex Medium Glucose contains: peptone 2 g/L, yeast extract 5 g/L and glucose 10 g/L in osmosed water: solution sterilized by autoclaving (15 minutes at 120° C.). To this solution are added the following solutions: MOPS buffer solution (10×) pH7 [acid MOPS 400 mM, $NH_4Cl$ 200 mM, NaOH 100 mM, KOH 100 mM, $CaCl_2$ 5 μM, $Na_2SO_4$ 2.76 mM, $MgCl_2$ 5.28 mM]; micronutrients (10000×) [$(NH_4)_6(Mo_7)24$ 300 mM, $H_3BO_3$ 4 mM, $CoCl_2$ 0.3 mM, $CuSO_4$ 0.1 mM, $MnCl_2$ 2.5 mM, $ZnSO_4$ 0.1 mM]; $FeCl_3$(100×) 2 mM in $C_6H_5Na_3O_7$ 20 mM; $K_2HPO_4$ 1 g/L: solutions sterilized by filtration (0.2 μm).

Defined Medium contains: carbon source 10 g/L in osmosed water: solution sterilized by autoclaving (15 minutes at 120° C.). To this solution are added the following solutions: MOPS buffer solution (10×) pH7 [acid MOPS 400 mM, $NH_4Cl$ 200 mM, NaOH 100 mM, KOH 100 mM, $CaCl_2$ 5 μM, $Na_2SO_4$ 2.76 mM, $MgCl_2$ 5.28 mM]; micronutrients (10000×) [$(NH_4)_6(Mo_7)24$ 300 mM, $H_3BO_3$ 4 mM, $CoCl_2$ 0.3 mM, $CuSO_4$ 0.1 mM, $MnCl_2$ 2.5 mM, $ZnSO_4$ 0.1 mM]; $FeCl_3$(100×) 2 mM in $C_6H_5Na_3O_7$ 20 mM; $K_2HPO_4$ 1 g/L: solutions sterilized by filtration (0.2 μm).

To these culture mediums, except for wild type strains, chloramphenicol is added before the seeding: 3 μg/mL the culture medium.

Cultures are performed both in aerobiosis and anaerobiosis (Biomerieux, Genbag).

Cultures in aerobiosis condition are left in an incubator, at 30° C., under agitation, for 7 days. The cultures are then centrifuged for 10 minutes at 4000 rpm. Supernatants are filtered (0.2 μm), poured into other tubes, and placed at −80° C.

Cultures in anaerobiosis condition are left in an incubator, at 30° C., for 4 weeks. The cultures are then centrifuged for 10 minutes at 4000 rpm. Supernatants are filtered (0.2 μm), poured into other tubes, and placed at −80° C.

Gas Chromatography FID analysis (Varian CP-WAX 57 CB 25 m*0.32 mm column) was used to quantify alcohols. Organic acids were quantified by Capillary Electrophoresis (5 mM 2,6-pyridinedicarboxylic acid 0.5 mM Cetyltrimethylammonium bromide; 5.6 pH adjusted buffers/61 cm length, 50 μm diameter capillary Agilent). Residual glucose was quantified by HPLC coupled with refractometry (Phenomenex LUNA 3 μm $NH_2$ 100 A 150*4.6 mm column, acetonitrile/$H_2O$ 85:15 mobile phase).

Example 1. *Deinococcus radiodurans* R1 L-Lactate Dehydrogenase (LDH) Deletion

LDH-mutants of the wild type *Deinococcus radiodurans* R1 (*D. radiodurans*) were produced as follows.
a. Construct for LDH Deletion (pDR-LDHdel)

We created a new construct named pDR-LDHdel for the partial deletion of the LDH gene (DR_2364) in wild type *D. radiodurans* (see FIG. 1). For this, we used the LITMUS28i backbone which is replicative in *E. coli* but not in *D. radiodurans*. A synthesized DNA insert was cloned in LITMUS28i; this insert is made of a chloramphenicol resistance ($Cam^R$) cassette (1344 nucleotides) and of 5' and 3' flanking homologous regions (537 nucleotides and 615 nucleotides) placed respectively upstream and downstream of this cassette (FIG. 2). The pDR-LDHdel construct was built to replace 589 nucleotides of LDH gene (some of the 589 nucleotides encoding for residues involved in catalysis) by the $Cam^R$ cassette.
b. Creation of LDH Deficient Mutants

*D. radiodurans* wild type was transformed with pDR-LDHdel following the procedure described in Materials and Methods, in order to create knockout mutants. The transformants were selected on chloramphenicol supplemented TGY medium. Replacement of part of the LDH gene by the chloramphenicol resistance cassette (FIG. 3) was controlled by PCR using appropriate primers annealing on the chloramphenicol cassette. Two double crossover integrant clones named 03-04/8-1 and 03-04/11-2 were selected for metabolites analysis (Table 1).

Upon homologous recombination, the resulting bacterium contains a deletion of 589 nucleotides, which are replaced by the $Cam^R$ cassette. The genomic regions of 03-04/8-1 and 03-04/11-2 where part of the LDH gene was replaced by the $Cam^R$ cassette were partially sequenced.

Example 2. Pyruvate Decarboxylase and Alcohol Dehydrogenase Production in *D. radiodurans*

*D. radiodurans* strains producing pyruvate decarboxylase (ZmPDC) and alcohol dehydrogenase (ZmADH) from *Zymomonas mobilis* were created as follows.
a. Creation of Constructs Carrying Genes for Ethanol Production Four constructs were created in order to produce ethanol in *D. radiodurans* cells (see FIG. 2).

For the first construct named pI3-DR-P-PDC-ADH, the pyruvate decarboxylase gene (ZmPDC, ZMO1360) and the alcohol dehydrogenase II gene (ZmADH, ZMO1596) from *Zymomonas mobilis* subsp. *Mobilis* ZM4 (FIG. 4) were placed in operon and cloned into BamHI and SalI of the *D. radiodurans* replicative pI3 plasmid (Masters and Minton, 1992) (see FIG. 5). pI3 vector confers chloramphenicol resistance in *D. radiodurans*. A region of 432 base pairs located upstream of the translational start codon of the elongation factor TU tufA (DR_0309) and containing a promoter activity (Lecointe et al, 2004) was placed before the ZmPDC-ADH operon. A spacer is present between the ZmPDC and the ZmADH genes with a ribosomal binding sequence (RBS) from the *D. radiodurans* operon groESL (Meima et al, 2001) placed before the translational initiation codon of ZmADH. The *D. radiodurans* transcription terminator Term116 (Lecointe et al, 2004) was placed downstream of the ZmADH gene. A second construct derived from pI3-DR-P-PDC-ADH was created and is named pI3-DR-P-PDCtag-ADHtag. In this construct, a his-tag (6 histidines) was placed in C-terminus of ZmPDC and a c-myc tag (EQKLISEEDL) was placed in C-terminus of ZmADH (FIG. 5).

For the construct pI3-DR-P-PDC-P-ADH, a region containing a putative transcription terminator named Term85 was placed downstream of the ZmPDC gene and the 234 nucleotides located upstream of the translational start codon of the elongation factor TU turn (DR_2050) (which corresponds to the tufB promoter region, Lecointe et al, 2004) were placed between Term85 and the ZmADH gene (FIG. 5). The last construct is derived from pI3-P-PDC-P-ADH and is named pI3-DR-P-PDCtag-P-ADHtag; in this vector, a his tag (6 histidines) was placed in C-terminus of ZmPDC gene and a c-myc tag (EQKLISEEDL) was placed in C-terminus of ZmADH gene (FIG. 5).

b. Creation of *D. radiodurans* Strains Producing ZmPDC and ZmADH

*D. radiodurans* competent cells were transformed with the different constructs carrying the ZmPDC and ZmADH genes. The transformants were selected for chloramphenicol resistance. The presence of the plasmid was controlled by PCR amplification with specific primers or enzymatic digestions of the construct extracted from *D. radiodurans* clones. For each of the 4 constructs, two clones were used for metabolic studies (Table 1).

Example 3. Creation of Integrative *Deinococcus radiodurans* LDH-Mutants Producing ZmPDC and ZmADH 589 nucleotides of the LDH gene (DR_2364) were replaced in wild type *D. radiodurans* by a chloramphenicol resistance cassette followed by ZmPDC and ZmADH genes respectively under the control of PtufA and PtufB promoters.

In order to create this PDC+ADH+LDH− mutant, the 3 following nucleotidic sequences were amplified by PCR:
- the 5' flanking homologous region followed by a chloramphenicol resistance cassette were amplified with primers EG31F and EG32R (see list below) using pDR-LDHdel as a template
- P-PDC-P-ADH sequence was amplified with primers EG33F and EG34R (see list below) using pI3-P-PDC-P-ADH as a template
- the 3' flanking homologous region was amplified with primers EG35F and EG36R (see list below) using pDR-LDHdel as a template List of Primers:

```
EG31F SEQ ID NO: 5   5'-TTCCCCGCCTGGGTATCACGTC-3'

EG32R SEQ ID NO: 6   5'-CTCGGATCCTTCACAGTTCTCCGCCCCCTCC-3'

EG33F SEQ ID NO: 7   5'-GAGGGATCCGTCGGGTGTCGAGCATCGTGATC-3'

EG34R SEQ ID NO: 8   5'-CCTCCTGCAGTTGTTTTTGCAATAAACAAAAACAAAAAAACCCCC-3'

EG35F SEQ ID NO: 9   5'-GAGACTGCAGTGGAACGAGCAGGTGCGCGCC-3'

EG36R SEQ ID NO: 10  5'-ACGCGTGAGCAAAGGGCGGCG-3'
```

The ligation product of these 3 amplicons was used to transform *D. radiodurans* to obtain the mutant PDC+ADH+ LDH− (FIG. 8). The transformants were selected for chloramphenicol resistance. Partial deletion of the LDH gene, genomic insertion of the chloramphenicol resistance gene and of ZmPDC and ZmADH genes were controlled by PCR using appropriate primers. Two double crossover integrant clones named 18-06/1-1 and 18-06/1-3 were selected for metabolites analysis (Tables 1 and 4).

Example 4. *Deinococcus radiodurans* R1 Recombinants: Alcohol Dehydrogenase Activity We determined the aldehyde production and ADH activity with a colorimetric test according to Conway and collaborators (1987b) in different recombinants transformed with plasmids having ZmPDC and ZmADH genes. This test is based on the formation of a violet Schiff base formed after interaction of acetaldehyde produced by ADH from ethanol and a leuco dye. As shown on FIG. 6, recombinants of this invention are colored in violet after 2 to 3 hours of incubation at 37° C. on LB agar plates supplemented with ethanol, pararosaniline and sodium bisulfite. This coloration shows an ADH activity in each clone of the recombinants transformed with plasmid pI3-DR-P-PDC-P-ADH or pI3-DR-P-PDCtag-P-ADHtag. In these recombinants, ZmADH gene transcription was controlled by the tufB promoter.

Example 5. *Deinococcus radiodurans* R1 Recombinants: Metabolite Production

Metabolites produced by recombinants of the invention were analysed.

We could detect a change in metabolites produced by recombinants of this invention (e.g., clones 24-03/4-2, 03-04/4-1, 03-04/4-2), as compared to the wild-type or control recombinant transformed with the mock vector backbone pI3 (see Tables 2-5). In particular, a production of ethanol was detected, under different culture conditions, while the parent strain does not produce ethanol.

TABLE 1

Name of Recombinants

| Transformed strain | Replicative or integrative construct | Name of the clones |
|---|---|---|
| *D. radiodurans* R1 | No construct | 24-03/1-2 |
|  |  | 03-04/1-1 |
|  |  | 20-04/1-2 |
| *D. radiodurans* R1 | pDR-LDHdel | 03-04/8-1 |
|  |  | 03-04/11-2 |
| *D. radiodurans* R1 | pI3 | 24-03/2-2 |
|  |  | 03-04/2-1 |
|  |  | 20-04/3-1 |

TABLE 1-continued

Name of Recombinants

| Transformed strain | Replicative or integrative construct | Name of the clones |
|---|---|---|
| *D. radiodurans* R1 | pI3-DR-P-PDCtag-ADHtag | 24-03/4-2 |
|  |  | 24-03/5-2 |
| *D. radiodurans* R1 | pI3-DR-P-PDC-ADH | 20-04/4-3 |
|  |  | 20-04/5-4 |
| *D. radiodurans* R1 | pI3-DR-P-PDCtag-P-ADHtag | 03-04/5-1 |
|  |  | 03-04/6-1 |
| *D. radiodurans* R1 | pI3-DR-P-PDC-P-ADH | 03-04/4-1 |
|  |  | 03-04/4-2 |
| *D. radiodurans* R1 | PCR products | 18-06/1-1 |
|  |  | 18-06/1-3 |

TABLE 2

*Deinococcus radiodurans* R1 recombinants: Metabolites production in Complex Medium Glucose ("CM") under aerobiosis culture conditions

| Strain | Clone | Acid production (g/L) | | | ethanol (%)* | consumed glucose (g/L) |
|---|---|---|---|---|---|---|
| | | Succinate | acetate | lactate | | |
| Drad R1 WT | 24-03/1-2 | 0.43 | 0.21 | 0 | 0 | 0 |
| Drad R1 pI3 | 24-03/2-2 | 0.43 | 0.23 | 0 | 0 | 0.6 |
| Drad R1 pI3 DR-P-PDCtag-ADH tag | 24-03/4-2 | 0.31 | 0.17 | 0 | 0.005 | 1.2 |
| Drad R1 WT | 03-04/1-1 | 0.42 | 0.2 | 0 | 0 | 0 |
| Drad R1 pI3 | 03-04/2-1 | 0.37 | 0.2 | 0 | 0 | 0.9 |
| Drad R1 pI3 DR-P-PDC-P-ADH | 03-04/4-1 | 0.25 | 0.14 | 0 | 0.016 | 0.2 |
| Drad R1 pI3 DR-P-PDC-P-ADH | 03-04/4-2 | 0.27 | 0.14 | 0.02 | 0.016 | 0.2 |
| Drad R1 pI3 DR-P-PDCtag-P-ADHtag | 03-04/5-1 | 0.29 | 0.11 | 0 | 0.006 | 0.4 |
| Drad R1 pI3 DR-P-PDCtag-P-ADHtag | 03-04/6-1 | 0.33 | 0.14 | 0 | 0.006 | 0.3 |
| Drad R1 pDR-LDHdel | | 0.28 | 0.18 | 0 | 0 | 0.4 |
| Drad R1 pDR-LDHdel | | 0.33 | 0.39 | 0 | 0 | 0 |

*% ethanol designates g ethanol per g of culture medium (i.e., typically 1% ethanol = 1 g ethanol/100 g medium = 10 g ethanol/L).
For each clone, cultures are performed in triplicates.

TABLE 3

*Deinococcus radiodurans* R1 recombinants: Metabolites production in Complex Medium Glucose ("CM") under aerobiosis culture conditions

| | Acid production (g/L) | | | ethanol (%) | consumed glucose (g/L) |
|---|---|---|---|---|---|
| | succinate | acetate | lactate | | |
| Drad R1 Wild Type | 0.66 | 0.64 | 0 | 0 | 3.13 |
| Drad R1 pI3 (empty plasmid) | 0.53 | 0.41 | 0 | 0 | 1.77 |
| Drad R1 pI3 DR-P-PDC-ADH | 0.46 | 0.51 | 0 | 0.005 | 1.8 |
| Drad R1 pI3 DR-P-PDC-ADH | 0.49 | 0.5 | 0 | 0.006 | 1.85 |

For each clone, cultures are performed in triplicates.

TABLE 4

*Deinococcus radiodurans* integrative R1 recombinants: Metabolites production in Complex Medium Glucose ("CM") under aerobiosis culture conditions

| | Acid production (g/L) | | | ethanol (%) | consumed glucose (g/L) |
|---|---|---|---|---|---|
| | succinate | acetate | lactate | | |
| Drad R1 Wild Type | 0.44 | 0.53 | 0.32 | 0 | 0.55 |
| Drad R1 CamR PDC + ADH + LDH– | 0.46 | 0.55 | 0 | 0.026 | 0.6 |
| Drad R1 CamR PDC + ADH + LDH– | 0.4 | 0.4 | 0 | 0.026 | 1.08 |

For each clone, cultures are performed in triplicates.

TABLE 5

*Deinococcus radiodurans* R1 recombinants: Metabolites production in Defined Medium Sucrose ("DM") under aerobiosis culture conditions

| | Acid production (g/L) | | | | ethanol (%) |
|---|---|---|---|---|---|
| | succinate | acetate | lactate | Formate | |
| Drad R1 WT | 0.02 | 0.11 | 0.03 | 0.04 | 0 |
| Drad R1 pI3 | 0.02 | 0.11 | 0.03 | 0.04 | 0 |
| Drad R1 pI3 DR-P-PDC-P-ADH | 0 | 0 | 0 | 0 | 0.009 |
| Drad R1 pI3 DR-P-PDC-P-ADH | 0.02 | 0.13 | 0 | 0 | 0.012 |
| Drad R1 pI3 DR-P-PDCtag-P-ADHtag | 0.01 | 0.17 | 0.07 | 0 | 0.007 |
| Drad R1 pI3 DR-P-PDCtag-P-ADHtag | 0 | 0.05 | 0 | 0 | 0.007 |

These results thus demonstrate that ethanol production can be induced or increased in stress-resistant bacteria by engineering new metabolic pathways. The results further show that LDH-defective strains are viable, and that the inactivation of this gene further increases ethanol production in the bacteria of the invention. Also, the results show the strains may use different types of substrates and grow under different types of culture media to produce ethanol.

The recombinant strains of this invention thus combine the advantages of stress-resistance, culture conditions, substrate acceptance and metabolite production.

BIBLIOGRAPHY

Anderson A W, Nordon H C, Cain R F, Parrish G, Duggan D (1956) Studies on a radioresistant *micrococcus*. I. Isolation, morphology, cultural characteristics, and resistance to gamma radiation. Food Technol. 10, 575-578.

Brau B and Sahm H (1986) Cloning and expression of the structural gene for pyruvate decarboxylase of *Zymomonas mobilis* in *Escherichia coli*. Arch Microbiol. 144, 296-301.

Chandra Raj K, Ingram L O, Maupin-Furlow J A. (2001) Pyruvate decarboxylase: a key enzyme for the oxidative metabolism of lactic acid by *Acetobacter pasteurianus*. Arch Microbiol. 176, 443-451.

Conway T, Osman Y A, Konnan J I, Hoffmann E M, Ingram L O (1987a) Promoter and nucleotide sequences of the *Zymomonas mobilis* pyruvate decarboxylase. J Bacteriol 169, 949-954.

Conway T, Sewell G W, Osman Y A, Ingram L O (1987b) Cloning and sequencing of the alcohol dehydrogenase II gene from *Zymomonas mobilis*. J Bacteriol. 169, 2591-2597.

Coquelle N, Fioravanti E, Weik M, Vellieux F, Madern D (2007) Activity, stability and structural studies of lactate dehydrogenases adapted to extreme thermal environments. J Mol Biol 374, 547-562.

Daly M J, Ouyang L, Fuchs P, Minton K W (1994) In vivo damage and recA-dependent repair of plasmid and chromosomal DNA in the radiation-resistant bacterium *Deinococcus radiodurans*. J Bacteriol. 176, 3508-3517.

Ingram L O, Conway T, Clark D P, Sewell G W, Preston J F (1987) Genetic engineering of ethanol production in *Escherichia coli*. Appl Environ Microbiol. 53, 2420-2425.

Lecointe F, Coste G, Sommer S, Bailone A (2004) Vectors for regulated gene expression in the radioresistant bacterium *Deinococcus radiodurans*. Gene 336,25-35.

Liu S, Dien B S, Nichols N N, Bischoff K M, Hughes S R, Cotta M A. (2007) Coexpression of pyruvate decarboxylase and alcohol dehydrogenase genes in *Lactobacillus brevis*. FEMS Microbiol Lett. 274, 291-297.

Lowe S E and Zeikus J G (1992) Purification and characterization of pyruvate decarboxylase from *Sarcina ventriculi*. J Gen Microbiol. 138, 803-807.

Masters C I and Minton K W (1992) Promoter probe and shuttle plasmids for *Deinococcus radiodurans*. Plasmid 28, 258-261.

Meima R and Lidstrom M E (2000) Characterization of the minimal replicon of a cryptic *Deinococcus radiodurans* SARK plasmid and development of versatile *Escherichia coli-D. radiodurans* shuttle vectors. Appl Environ Microbiol. 66, 3856-3867.

Meima R, Rothfuss H M, Gewin L, Lidstrom M E (2001) Promoter cloning in the radioresistant bacterium *Deinococcus radiodurans*. J Bacteriol. 183, 3169-3175.

Narumi I and Watanabe H (1996) Sequence analysis of the L-lactate dehydrogenase-encoding gene of *Deinococcus radiodurans*, a suitable mesophilic counterpart for *Thermus*. Gene 172, 117-119.

Neale A D, Scopes R K, Wettenhall R E, Hoogenraad N J. (1987) Nucleotide sequence of the pyruvate decarboxylase gene from *Zymomonas mobilis*. Nucleic Acids Res. 15, 1753-1761.

Raj K C, Talarico L A, Ingram L O, Maupin-Furlow J A. (2002) Cloning and characterization of the *Zymobacter palmae* pyruvate decarboxylase gene (pdc) and comparison to bacterial homologues. Appl Environ Microbiol. 68, 2869-2876.

Talarico L A, Gil M A, Yomano L P, Ingram L O, Maupin-Furlow J A. (2005) Construction and expression of an ethanol production operon in Gram-positive bacteria. Microbiol. 151, 4023-4031.

We claim:

1. A recombinant *Deinococcus* bacterium comprising a recombinant nucleic acid construct encoding a pyruvate decarboxylase (PDC) and an alcohol dehydrogenase (ADH), wherein the PDC and ADH coding sequences are placed in an operon in the recombinant nucleic acid construct, and wherein said recombinant nucleic acid construct is integrated into the genome of the bacterium.

2. The bacterium of claim 1, wherein said bacterium has a modified genome containing an at least partially inactive lactate dehydrogenase (LDH) gene.

3. The bacterium of claim 2, wherein the LDH gene is deleted all or in part and does not encode a functional protein.

4. The bacterium of claim 2, wherein the LDH gene has been at least partially inactivated by homologous recombination, gene replacement or targeted mutagenesis.

5. The bacterium of claim 1, wherein the genome of said bacterium lacks at least 589 consecutive nucleotides of the LDH gene.

6. The bacterium of claim 1, wherein said *Deinococcus* bacterium is selected from *D. radiodurans, D. geothermalis, D. murrayi, D. cellulosilyticus* or *D. deserti*.

7. The bacterium of claim 1, wherein said bacterium is a thermophilic *Deinococcus* bacterium.

8. A method of producing a biofuel comprising cultivating a bacterium of claim 1 in the presence of an appropriate substrate, and collecting the biofuel.

9. The method of claim 8, wherein said cultivating is performed at a temperature of about 40° C. or more, under acid pH conditions, and/or is at least partially viable in the presence of ethanol.

10. The method of claim 8, wherein the biofuel is a first generation biofuel selected from vegetable oil, biodiesel, bioalcohol, biogas, syngas and solid biofuel, or a second generation biofuel produced from non-food crops, biomass waste, stalks of wheat, corn and wood.

11. The method of claim 10, wherein said bioalcohol is ethanol, propanol or butanol.

12. A method for producing a recombinant bacterium according to claim 1, said method comprising:
   a) providing a *Deinococcus* bacterium;
   b) introducing into said bacterium a recombinant nucleic acid molecule encoding PDC and ADH, wherein the PDC and ADH coding sequences are placed in an operon in the recombinant nucleic acid molecule, and wherein said recombinant nucleic acid molecule is integrated into the genome of the bacterium; and
   c) optionally further treating the bacterium to reduce activity of the LDH gene and selecting a bacterium having an at least partially inactivated LDH gene.

13. A recombinant *Deinococcus* bacterium, wherein said bacterium contains a recombinant nucleic acid construct encoding a pyruvate decarboxylase (PDC) and an alcohol dehydrogenase (ADH), wherein the PDC and ADH coding sequences are placed in an operon in the recombinant nucleic acid construct, and wherein said recombinant nucleic acid construct is integrated into the genome of the bacterium in place of an endogenous LDH gene.

14. A method for producing ethanol comprising cultivating a bacterium of claim 13 in the presence of an appropriate substrate, and collecting ethanol.

15. The recombinant *Deinococcus* bacterium according to claim 1, wherein said recombinant nucleic acid construct comprises pI3-DR-P-PDC-ADH.

16. The recombinant *Deinococcus* bacterium according to claim 1, wherein said recombinant nucleic acid construct comprises a pyruvate decarboxylase gene (PDC) and an alcohol dehydrogenase (ADH) gene in an operon, said PDC gene and said ADH gene being separated by a nucleic acid spacer sequence that contains a ribosomal binding sequence and said recombinant nucleic acid construct comprises a termination sequence after said PDC gene and said ADH gene.

17. The method of claim 11, wherein said biofuel is ethanol and said substrate comprises plant biomass.

18. The method of claim 8, wherein said substrate comprises plant biomass.

19. A method for producing ethanol comprising cultivating a bacterium of claim 1 in the presence of an appropriate substrate, and collecting ethanol.

20. The method of claim 19, wherein said substrate comprises plant biomass.

21. The method of claim 19, wherein said substrate is a culture medium comprising glucose.

22. The method of claim 8, wherein said substrate is a culture medium comprising glucose.

23. The bacterium of claim 1, wherein said recombinant nucleic acid construct comprises a tufA promoter operably linked to the PDC coding sequence.

* * * * *

UNITED STATES PATENT AND TRADEMARK OFFICE
CERTIFICATE OF CORRECTION

PATENT NO. : 9,725,741 B2
APPLICATION NO. : 14/713248
DATED : August 8, 2017
INVENTOR(S) : Jacques Biton and Esther Gerber Page 1 of 1

It is certified that error appears in the above-identified patent and that said Letters Patent is hereby corrected as shown below:

In the Specification

Column 12,
Line 64, "TU turn" should read --TU tufB--.

Signed and Sealed this
Fifth Day of June, 2018

Andrei Iancu
*Director of the United States Patent and Trademark Office*

```
                        SEQUENCE LISTING

<160> NUMBER OF SEQ ID NOS: 10

<210> SEQ ID NO 1
<211> LENGTH: 537
<212> TYPE: DNA
<213> ORGANISM: artificial sequence
<220> FEATURE:
<223> OTHER INFORMATION: D. radiodurans R1 genome_ Sequences of 5'

<400> SEQUENCE: 1
ttccccgcct gggtatcacg tccccgccag agccgctctg taccttcggg gcatgaccca      60
gcccgtttct tcggttcccg gctcttccct ttccggcgca ggttttcagc gactgctggt     120
cgggatcgat ttctcgccct cgtcgttgca cgcccttgaa gtggcgcgga cccgctttcc     180
cggcgcgcgg ctgcggctcg cccacgtgac cgacgcccgc gcggtggcgg ctcccgacgt     240
ggtgggcggc gtcacgccga tcatgcccga cccggggctg ctgcaaacgc tcgaagacgc     300
cgattccaac cggctctcgg ggctgatccg cgacggtgag gaaagcgagc tgctcgtcgg     360
cgatcccatc acggggctgc tcgacgcggc ccgggcgtgg ggcgcggacc tgatcgtggt     420
cggcacccac ccgcagggcg cgctggaaca cttttttcatc ggcagcagcg ccgagaagct     480
ggtgggccgc agcgcggtgc cggtgctgtg cgtgccctcg ggagcacaca gatgaaa       537

<210> SEQ ID NO 2
<211> LENGTH: 615
<212> TYPE: DNA
<213> ORGANISM: artificial sequence
<220> FEATURE:
<223> OTHER INFORMATION: D. radiodurans R1 genome_ Sequences of 3'

<400> SEQUENCE: 2
tggaacgagc aggtgcgcgc caaaatcgat gagggcaccc gcaacgccgc cgccagcatc      60
```

|  |  |
|---|---|
| atcgagggca agcgggccac ctactacggc atcggcgcgg cgctcgcccg catcaccgag | 120 |
| gccgtgctgc gtgaccgccg cgccgtcctg accgtcagtg cgccgacccc cgaatacggc | 180 |
| gtgagcctca gcctgccgcg tgtcgtgggc cgtcaggggg tgctgtccac cctgcacccc | 240 |
| aagctgaccg cgcgacgagca acagaagctg aacagagtg ccggggtgct gcgcggcttc | 300 |
| aagcagcagc tcggcctgtg acgccgacgc tccagaccgt ctacggcgag cgcagccgc | 360 |
| tcgactggct gtgcctcgcc ccccaccccg acgacgccga aatcggcgcg gcggcacgc | 420 |
| tgatccggct ggcgcaggcg ggccgggcag tggggattct ggaactcacg cgcggtgaaa | 480 |
| agggcaccca ggggacgccc gccgagcggc aggccgagtg cgtggcggcg gcccgcctga | 540 |
| tggacctgag ctggcgcggc caactcgggc tgcccgatgg ggaactcgcc gacacgccgc | 600 |
| cctttgctca cgcgt | 615 |

<210> SEQ ID NO 3
<211> LENGTH: 1707
<212> TYPE: DNA
<213> ORGANISM: artificial sequence
<220> FEATURE:
<223> OTHER INFORMATION: Nucleic acid sequence of ZmPDC gene

<400> SEQUENCE: 3

|  |  |
|---|---|
| atgagttata ctgtcggtac ctatttagcg gagcggcttg tccagattgg tctcaagcat | 60 |
| cacttcgcag tcgcgggcga ctacaacctc gtccttcttg acaacctgct tttgaacaaa | 120 |
| aacatggagc aggtttattg ctgtaacgaa ctgaactgcg gtttcagtgc agaaggttat | 180 |
| gctcgtgcca aggcgcagc agcagccgtc gttacctaca cgtcggtgc gctttccgca | 240 |
| tttgatgcta tcggtggcgc ctatgcagaa aaccttccgg ttatcctgat ctccggtgct | 300 |
| ccgaacaaca atgatcacgc tgctggtcac gtgttgcatc acgctcttgg caaaaccgac | 360 |
| tatcactatc agttggaaat ggccaagaac atcacggccg ccgctgaagc gatttacacc | 420 |
| ccggaagaag ctccggctaa aatcgatcac gtgattaaaa ctgctcttcg tgagaagaag | 480 |
| ccggtttatc tcgaaatcgc ttgcaacatt gcttccatgc cctgcgccgc tcctggaccg | 540 |
| gcaagcgcat tgttcaatga cgaagccagc gacgaagctt ctttgaatgc agcggttgaa | 600 |
| gaaaccctga attcatcgc caaccgcgac aaagttgccg tcctcgtcgg cagcaagctg | 660 |
| cgcgcagctg tgctgaaga gctgctgtc aaatttgctg atgctctcgg tggcgcagtt | 720 |
| gctaccatgg ctgctgcaaa aagcttcttc ccagaagaaa accccgcatta catcggcacc | 780 |
| tcatggggtg aagtcagcta tccgggcgtt gaaaagacga tgaaagaagc cgatgcggtt | 840 |
| atcgctctgg ctcctgtctt caacgactac tccaccactg gttggacgga tattcctgat | 900 |
| cctaagaaac tggttctcgc tgaaccgcgt tctgtcgtcg ttaacggcat tcgcttcccc | 960 |
| agcgtccatc tgaaagacta tctgacccgt ttggctcaga aagtttccaa gaaaaccggt | 1020 |
| gcattggact tcttcaaatc cctcaatgca ggtgaactga gaaagccgc tccggctgat | 1080 |
| ccgagtgctc cgttggtcaa cgcagaaatc gcccgtcagg tcgaagctct tctgaccccg | 1140 |
| aacacgacgg ttattgctga aaccggtgac tcttggttca atgctcagcg catgaagctc | 1200 |
| ccgaacggtg ctcgcgttga atatgaaatg cagtggggtc acattggttg gtccgttcct | 1260 |
| gccgccttcg gttatgccgt cggtgctccg gaacgtcgca acatcctcat ggttggtgat | 1320 |
| ggttccttcc agctgacggc tcaggaagtc gctcagatgg ttcgcctgaa actgccggtt | 1380 |
| atcatcttct tgatcaataa ctatggttac accatcgaag ttatgatcca tgatggtccg | 1440 |
| tacaacaaca tcaagaactg ggattatgcc ggtctgatgg aagtgttcaa cggtaacggt | 1500 |

-continued

| | |
|---|---|
| ggttatgaca gcggtgctgg taaaggcctg aaggctaaaa ccggtggcga actggcagaa | 1560 |
| gctatcaagg ttgctctggc aaacaccgac ggcccaaccc tgatcgaatg cttcatcggt | 1620 |
| cgtgaagact gcactgaaga attggtcaaa tggggtaagc gcgttgctgc cgccaacagc | 1680 |
| cgtaagcctg ttaacaagct cctctag | 1707 |

```
<210> SEQ ID NO 4
<211> LENGTH: 1152
<212> TYPE: DNA
<213> ORGANISM: artificial sequence
<220> FEATURE:
<223> OTHER INFORMATION: Nucleic acid sequence of ZmADH II gene

<400> SEQUENCE: 4
```

| | |
|---|---|
| atggcttctt caactttta tattcctttc gtcaacgaaa tgggcgaagg ttcgcttgaa | 60 |
| aaagcaatca aggatcttaa cggcagcggc tttaaaaatg cgctgatcgt ttctgatgct | 120 |
| ttcatgaaca atccggtgt tgtgaagcag gttgctgacc tgttgaaagc acagggtatt | 180 |
| aattctgctg tttatgatgg cgttatgccg aacccgactg ttaccgcagt tctggaaggc | 240 |
| cttaagatcc tgaaggataa caattcgac ttcgtcatct ccctcggtgg tggttctccc | 300 |
| catgactgcg ccaaagccat cgctctggtc gcaaccaatg gtggtgaagt caaagactac | 360 |
| gaaggtatcg acaaatctaa gaaacctgcc ctgcctttga tgtcaatcaa cacgacggct | 420 |
| ggtacggctt ctgaaatgac gcgtttctgc atcatcactg atgaagtccg tcacgttaag | 480 |
| atggccattg ttgaccgtca cgttaccccg atggtttccg tcaacgatcc tctgttgatg | 540 |
| gttggtatgc caaaaggcct gaccgccgcc accggtatgg atgctctgac ccacgcattt | 600 |
| gaagcttatt cttcaacggc agctactccg atcaccgatg cttgcgcttt gaaagcagct | 660 |
| tccatgatcg ctaagaatct gaagaccgct tgcgacaacg gtaaggatat gccggctcgt | 720 |
| gaagctatgg cttatgccca attcctcgct ggtatggcct tcaacaacgc ttcgcttggt | 780 |
| tatgtccatg ctatggctca ccagttgggc ggttactaca acctgccgca tggtgtctgc | 840 |
| aacgctgttc tgcttccgca tgttctggct tataacgcct ctgtcgttgc tggtcgtctg | 900 |
| aaagacgttg gtgttgctat gggtctcgat atcgccaatc tcggtgataa agaaggcgca | 960 |
| gaagccacca ttcaggctgt tcgcgatctg gctgcttcca ttggtattcc agcaaacctg | 1020 |
| accgagctgg gtgctaagaa agaagatgtg ccgcttcttg ctgaccacgc tctgaaagat | 1080 |
| gcttgtgctc tgaccaaccc gcgtcagggt gatcagaaag aagttgaaga actcttcctg | 1140 |
| agcgctttct aa | 1152 |

```
<210> SEQ ID NO 5
<211> LENGTH: 22
<212> TYPE: DNA
<213> ORGANISM: artificial sequence
<220> FEATURE:
<223> OTHER INFORMATION: EG31F

<400> SEQUENCE: 5
```

| | |
|---|---|
| ttccccgcct gggtatcacg tc | 22 |

```
<210> SEQ ID NO 6
<211> LENGTH: 31
<212> TYPE: DNA
<213> ORGANISM: artificial sequence
<220> FEATURE:
<223> OTHER INFORMATION: EG32R
```

```
<400> SEQUENCE: 6
ctcggatcct tcacagttct ccgccccctc c                              31

<210> SEQ ID NO 7
<211> LENGTH: 32
<212> TYPE: DNA
<213> ORGANISM: artificial sequence
<220> FEATURE:
<223> OTHER INFORMATION: EG33F

<400> SEQUENCE: 7
gagggatccg tcgggtgtcg agcatcgtga tc                             32

<210> SEQ ID NO 8
<211> LENGTH: 45
<212> TYPE: DNA
<213> ORGANISM: artificial sequence
<220> FEATURE:
<223> OTHER INFORMATION: EG34R

<400> SEQUENCE: 8
cctcctgcag ttgtttttgc aataaacaaa acaaaaaaa ccccc                45

<210> SEQ ID NO 9
<211> LENGTH: 31
<212> TYPE: DNA
<213> ORGANISM: artificial sequence
<220> FEATURE:
<223> OTHER INFORMATION: EG35F

<400> SEQUENCE: 9
gagactgcag tggaacgagc aggtgcgcgc c                              31

<210> SEQ ID NO 10
<211> LENGTH: 21
<212> TYPE: DNA
<213> ORGANISM: artificial sequence
<220> FEATURE:
<223> OTHER INFORMATION: EG36R

<400> SEQUENCE: 10
acgcgtgagc aaagggcggc g                                         21
```